US010188378B2

(12) United States Patent
Lunn et al.

(10) Patent No.: US 10,188,378 B2
(45) Date of Patent: Jan. 29, 2019

(54) MICROANCHOR

(71) Applicant: Smith & Nephew, Inc., Memphis, TN (US)

(72) Inventors: Rick Lunn, Kingston, MA (US); Timothy Young, Natick, MA (US); Mark Edwin Housman, Westford, MA (US); John Slusarz, Hopedale, MA (US); Paul Alexander Torrie, Marblehead, MA (US); Wei Li Fan, Boston, MA (US); Steven Astorino, Norfold, MA (US)

(73) Assignee: Smith & Nephew, Inc., Memphis, TN (US)

( * ) Notice: Subject to any disclaimer, the term of this patent is extended or adjusted under 35 U.S.C. 154(b) by 272 days.

(21) Appl. No.: 14/199,661

(22) Filed: Mar. 6, 2014

(65) Prior Publication Data
US 2014/0257385 A1    Sep. 11, 2014

Related U.S. Application Data

(60) Provisional application No. 61/773,613, filed on Jun. 3, 2013.

(51) Int. Cl.
*A61B 17/04* (2006.01)

(52) U.S. Cl.
CPC .. *A61B 17/0401* (2013.01); *A61B 2017/0403* (2013.01); *A61B 2017/0409* (2013.01); *A61B 2017/0412* (2013.01); *A61B 2017/0414* (2013.01); *A61B 2017/0445* (2013.01); *A61B 2017/0448* (2013.01); *A61B 2017/0464* (2013.01)

(58) Field of Classification Search
CPC ............ A61B 17/0401; A61B 17/7022; A61B 17/7032; A61B 2017/044–2017/0443; A61B 17/0466; A61B 2017/0459; A61B 2017/0461
USPC .......................... 606/232, 300–321; 411/999
See application file for complete search history.

(56) References Cited

U.S. PATENT DOCUMENTS

| 332,701   | A | 12/1885 | Craig   |
|-----------|---|---------|---------|
| 768,283   | A | 8/1904  | Jenkins |
| 3,716,058 | A | 2/1973  | Tanner  |

(Continued)

FOREIGN PATENT DOCUMENTS

| EP | 0686373 A1 | 12/1995 |
|----|------------|---------|
| EP | 0829233 A1 | 3/1998  |

(Continued)

OTHER PUBLICATIONS

International Preliminary Report of PCT/US2014/021203, dated Sep. 17, 2015.

(Continued)

*Primary Examiner* — Ryan J Severson
*Assistant Examiner* — Charles Wei
(74) *Attorney, Agent, or Firm* — Burns & Levinson, LLP; Joseph M. Maraia

(57) ABSTRACT

Examples of a suture anchor having a small diameter and having a soft suture bridge or suture eyelet are described herein. The soft suture bridge/suture eyelet allows a repair suture to slide, which is desirable when tying knots. In some cases, the soft suture bridge/suture eyelet itself is made from a length of suture.

24 Claims, 28 Drawing Sheets

(56) References Cited

U.S. PATENT DOCUMENTS

| | | | |
|---|---|---|---|
| 4,537,185 A | 8/1985 | Stednitz | |
| 4,738,255 A | 4/1988 | Goble et al. | |
| 4,870,957 A | 10/1989 | Goble et al. | |
| 4,988,351 A | 1/1991 | Paulos et al. | |
| 5,100,417 A | 3/1992 | Cerier et al. | |
| 5,125,840 A | 6/1992 | Duerr et al. | |
| 5,139,520 A | 8/1992 | Rosenberg | |
| 5,156,616 A | 10/1992 | Meadows et al. | |
| 5,243,300 A | 9/1993 | Kubo | |
| 5,258,016 A * | 11/1993 | DiPoto | A61B 17/0401 606/104 |
| 5,370,662 A | 12/1994 | Stone et al. | |
| 5,383,905 A | 1/1995 | Golds et al. | |
| 5,411,506 A | 5/1995 | Goble et al. | |
| 5,417,712 A | 5/1995 | Whittaker et al. | |
| 5,423,860 A | 6/1995 | Lizardi et al. | |
| 5,464,427 A | 11/1995 | Curtis et al. | |
| 5,470,334 A | 11/1995 | Ross et al. | |
| 5,472,452 A | 12/1995 | Trott | |
| 5,486,197 A | 1/1996 | Le et al. | |
| 54,804,403 | 1/1996 | Lee et al. | |
| 5,505,735 A | 4/1996 | Li | |
| 5,554,191 A | 9/1996 | Lahille | |
| 5,573,548 A | 11/1996 | Nazre et al. | |
| 5,584,835 A | 12/1996 | Greenfield | |
| 5,597,953 A | 1/1997 | Usanov et al. | |
| 5,662,654 A | 9/1997 | Thompson | |
| 5,690,676 A | 11/1997 | Dipoto et al. | |
| 5,702,397 A | 12/1997 | Goble et al. | |
| 5,718,717 A * | 2/1998 | Bonutti | A61B 17/0401 606/139 |
| 5,723,013 A | 3/1998 | Jeanson et al. | |
| 5,725,529 A | 3/1998 | Nicholson et al. | |
| 5,733,307 A * | 3/1998 | Dinsdale | A61B 17/0401 606/104 |
| 5,824,011 A * | 10/1998 | Stone | A61B 17/0401 606/232 |
| 5,827,285 A | 10/1998 | Bramlet | |
| 5,845,645 A * | 12/1998 | Bonutti | A61B 17/0401 128/898 |
| 5,899,920 A * | 5/1999 | DeSatnick | A61B 17/0401 606/232 |
| 5,935,129 A | 8/1999 | McDevitt et al. | |
| 5,948,001 A | 9/1999 | Larsen | |
| 5,957,953 A | 9/1999 | DiPoto et al. | |
| 5,993,459 A | 11/1999 | Larsen et al. | |
| 6,048,344 A | 4/2000 | Schenk | |
| 6,086,608 A | 7/2000 | Ek et al. | |
| 6,089,805 A | 7/2000 | Salmon | |
| 6,117,161 A | 9/2000 | Li et al. | |
| 6,123,711 A | 9/2000 | Winters | |
| 6,162,234 A | 12/2000 | Freedland et al. | |
| 6,168,598 B1 | 1/2001 | Martello | |
| 6,214,031 B1 | 4/2001 | Schmieding et al. | |
| 6,221,107 B1 | 4/2001 | Steiner et al. | |
| 6,355,043 B1 | 3/2002 | Adam | |
| 6,436,124 B1 | 8/2002 | Anderson et al. | |
| 6,511,499 B2 | 1/2003 | Schmieding et al. | |
| 6,517,542 B1 | 2/2003 | Papay et al. | |
| 6,533,816 B2 | 3/2003 | Sklar | |
| 6,544,281 B2 | 4/2003 | Elattrache et al. | |
| 6,554,830 B1 | 4/2003 | Chappius | |
| 6,613,053 B1 | 9/2003 | Collins | |
| 6,641,596 B1 | 11/2003 | Lizardi | |
| 6,648,903 B1 | 11/2003 | Pierson | |
| 6,656,183 B2 | 12/2003 | Colleran et al. | |
| 6,840,953 B2 | 1/2005 | Martinek | |
| 6,863,530 B2 | 3/2005 | McDevitt | |
| 6,916,321 B2 | 7/2005 | Teni-Huisen et al. | |
| 6,923,824 B2 | 8/2005 | Morgan et al. | |
| 7,090,690 B2 | 8/2006 | Foerster et al. | |
| 7,195,634 B2 | 3/2007 | Schmieding et al. | |
| 7,201,754 B2 | 4/2007 | Stewart et al. | |
| 7,322,978 B2 | 1/2008 | West, Jr. | |
| 7,588,587 B2 | 9/2009 | Barbieri et al. | |
| 7,695,495 B2 * | 4/2010 | Dreyfuss | A61B 17/0401 606/224 |
| 7,780,701 B1 | 8/2010 | Meridew et al. | |
| 7,828,820 B2 | 11/2010 | Stone et al. | |
| 7,919,890 B2 | 4/2011 | Taketsuna | |
| 7,995,388 B1 | 6/2011 | Jensen et al. | |
| 7,976,565 B1 | 7/2011 | Meridew | |
| 8,088,130 B2 * | 1/2012 | Kaiser | A61B 17/0401 606/139 |
| 8,202,295 B2 | 6/2012 | Kaplan | |
| 8,343,186 B2 | 1/2013 | Dreyfuss et al. | |
| 8,454,654 B2 | 6/2013 | Ferragamo et al. | |
| 8,486,120 B2 | 7/2013 | Shimko | |
| 8,623,052 B2 | 1/2014 | Dreyfuss et al. | |
| 8,663,279 B2 | 3/2014 | Burkhart | |
| 8,801,755 B2 | 5/2014 | Dreyfuss et al. | |
| 8,821,541 B2 | 9/2014 | Dreyfuss et al. | |
| 2001/0049528 A1 | 12/2001 | Kubota | |
| 2002/0049447 A1 | 4/2002 | Li | |
| 2002/0052629 A1 | 5/2002 | Morgan et al. | |
| 2002/0111653 A1 | 8/2002 | Foerster | |
| 2002/0147463 A1 | 10/2002 | Martinek | |
| 2002/0161404 A1 | 10/2002 | Steiner | |
| 2002/0169453 A1 | 11/2002 | Berger | |
| 2002/0177898 A1 | 11/2002 | Crozet | |
| 2003/0065361 A1 * | 4/2003 | Dreyfuss | A61B 17/0401 606/232 |
| 2003/0120309 A1 * | 6/2003 | Colleran | A61B 17/0401 606/232 |
| 2003/0225456 A1 | 12/2003 | Ek | |
| 2004/0106950 A1 | 6/2004 | Grafton et al. | |
| 2004/0136802 A1 | 7/2004 | Lin et al. | |
| 2004/0138706 A1 * | 7/2004 | Abrams | A61B 17/0401 606/232 |
| 2004/0210227 A1 | 10/2004 | Trail et al. | |
| 2004/0220575 A1 | 11/2004 | Biedermann et al. | |
| 2005/0075668 A1 | 4/2005 | Lizardi | |
| 2005/0107828 A1 | 5/2005 | Reese | |
| 2005/0192577 A1 | 9/2005 | Mosca et al. | |
| 2005/0222619 A1 | 10/2005 | Dreyfuss et al. | |
| 2005/0245932 A1 | 11/2005 | Fanton et al. | |
| 2005/0251137 A1 | 11/2005 | Ball | |
| 2006/0074422 A1 | 4/2006 | Story et al. | |
| 2006/0149258 A1 | 7/2006 | Sousa | |
| 2006/0167456 A1 | 7/2006 | Johnston et al. | |
| 2006/0200147 A1 | 9/2006 | Ensign et al. | |
| 2006/0229620 A1 | 10/2006 | Rothman et al. | |
| 2006/0235413 A1 | 10/2006 | Denham | |
| 2006/0246396 A1 | 11/2006 | Suttin et al. | |
| 2006/0247642 A1 | 11/2006 | Stone et al. | |
| 2006/0253119 A1 | 11/2006 | Berberich et al. | |
| 2006/0271054 A1 | 11/2006 | Sucec | |
| 2006/0276841 A1 | 12/2006 | Barbieri et al. | |
| 2006/0282081 A1 | 12/2006 | Fanton et al. | |
| 2006/0282083 A1 | 12/2006 | Fanton et al. | |
| 2007/0135841 A1 | 6/2007 | Dreyfuss | |
| 2007/0161985 A1 | 7/2007 | Demakas et al. | |
| 2007/0162025 A1 | 7/2007 | Tornier et al. | |
| 2007/0203498 A1 | 8/2007 | Gerber et al. | |
| 2007/0219557 A1 | 9/2007 | Bourque | |
| 2007/0225719 A1 | 9/2007 | Stone et al. | |
| 2007/0250064 A1 | 10/2007 | Darois et al. | |
| 2008/0009904 A1 | 1/2008 | Bourque et al. | |
| 2008/0103528 A1 * | 5/2008 | Zirps | A61B 17/0401 606/232 |
| 2008/0109038 A1 * | 5/2008 | Steiner | A61B 17/0401 606/232 |
| 2008/0125815 A1 | 5/2008 | Heaven et al. | |
| 2008/0147063 A1 | 6/2008 | Cauldwell et al. | |
| 2008/0154313 A1 | 6/2008 | Berberich | |
| 2008/0167660 A1 | 7/2008 | Moreau et al. | |
| 2008/0177330 A1 | 7/2008 | Ralph et al. | |
| 2008/0208253 A1 | 8/2008 | Dreyfuss et al. | |
| 2008/0215091 A1 | 9/2008 | Dreyfuss | |
| 2008/0249579 A1 | 10/2008 | Taylor | |
| 2008/0275469 A1 | 11/2008 | Fanton et al. | |
| 2008/0306511 A1 | 12/2008 | Cooper et al. | |
| 2009/0007654 A1 | 1/2009 | Niikawa et al. | |

(56) References Cited

U.S. PATENT DOCUMENTS

| | | | |
|---|---|---|---|
| 2009/0062854 A1* | 3/2009 | Kaiser | A61B 17/0401 606/232 |
| 2009/0076545 A1 | 3/2009 | Dimatteo et al. | |
| 2009/0082807 A1 | 3/2009 | Miller et al. | |
| 2009/0112270 A1 | 4/2009 | Lunn et al. | |
| 2009/0157124 A1 | 6/2009 | Ferragamo et al. | |
| 2009/0234387 A1 | 9/2009 | Miller et al. | |
| 2010/0016869 A1 | 1/2010 | Paulk et al. | |
| 2010/0016902 A1 | 1/2010 | Paulk et al. | |
| 2010/0106166 A1 | 4/2010 | Cropper et al. | |
| 2010/0130989 A1 | 5/2010 | Bourque et al. | |
| 2010/0152773 A1 | 6/2010 | Lunn et al. | |
| 2010/0217329 A1 | 8/2010 | Brown et al. | |
| 2010/0305576 A1* | 12/2010 | Ferguson | A61B 17/0401 606/104 |
| 2011/0112576 A1 | 5/2011 | Nguyen et al. | |
| 2012/0078300 A1 | 3/2012 | Mayer et al. | |
| 2012/0130424 A1* | 5/2012 | Sengun | A61B 17/0401 606/232 |
| 2012/0165867 A1* | 6/2012 | Denham | A61B 17/0401 606/232 |
| 2012/0165938 A1* | 6/2012 | Denham | A61B 17/0401 623/13.14 |
| 2012/0290003 A1* | 11/2012 | Dreyfuss | A61B 17/0401 606/232 |
| 2013/0096611 A1* | 4/2013 | Sullivan | A61B 17/0485 606/232 |
| 2013/0197577 A1 | 8/2013 | Wolf et al. | |
| 2015/0245831 A1* | 9/2015 | Sullivan | A61B 17/0485 606/232 |

FOREIGN PATENT DOCUMENTS

| | | | |
|---|---|---|---|
| EP | 1199035 A1 | 4/2002 | |
| EP | 1486171 A1 | 12/2004 | |
| EP | 1584297 A1 | 10/2005 | |
| EP | 1797825 A1 | 6/2007 | |
| EP | 1825817 A1 | 8/2007 | |
| EP | 2572648 A1 | 3/2013 | |
| JP | 50-121398 | 3/1949 | |
| JP | 54-26800 | 7/1952 | |
| JP | H10272142 A | 10/1998 | |
| JP | 2000-166937 | 6/2000 | |
| JP | 2001514545 | 9/2001 | |
| JP | 2005103272 A | 4/2004 | |
| JP | 200695301 A | 4/2006 | |
| JP | 2008029746 A | 2/2008 | |
| JP | 2008515605 A | 5/2008 | |
| JP | 2008520277 A | 6/2008 | |
| JP | 2008535544 A | 9/2008 | |
| JP | 2013509257 A | 3/2013 | |
| RU | 69730 U1 | 1/2008 | |
| WO | 199203979 A1 | 3/1992 | |
| WO | 1995016398 A1 | 6/1995 | |
| WO | 1995016399 A1 | 6/1995 | |
| WO | 199838938 A1 | 9/1998 | |
| WO | 200221999 A | 3/2002 | |
| WO | 2002021997 A2 | 3/2002 | |
| WO | 2002051325 A2 | 7/2002 | |
| WO | 2006044491 A2 | 4/2006 | |
| WO | 2006099109 A2 | 9/2006 | |
| WO | 2006122218 A2 | 11/2006 | |
| WO | 2007063285 A1 | 6/2007 | |
| WO | 2007078281 A2 | 7/2007 | |
| WO | 2009055800 A1 | 4/2009 | |
| WO | 2010121271 A1 | 10/2010 | |
| WO | 2011056701 A1 | 5/2011 | |

OTHER PUBLICATIONS

International Search Report and Written Opinion of PCT/US2014/021203, dated Jun. 4, 2014.
Patent Examination Report No. 1 dated Aug. 17, 2015 issued by IP Australia for Australian Patent Application No. 2012230845.
Patent Examination Report No. 1 dated Sep. 30, 2014 issued by IP Australia for Australian Patent Application No. 2009327446.
Decision of Rejection from related Japanese Patent Application No. 2011-540802, dated Jul. 14, 2014.
Communication pursuant to Article 94(3) from related European Patent Application No. 09771445.5-1303, dated Apr. 10, 2014.
First Office Action from related Japanese Patent Application No. 2011-540802, dated Dec. 24, 2013.
Second Office Action from related Chinese Patent Application No. 200980150612.6, dated Dec. 18, 2013.
International Search Report and Written Opinion for PCT/US2012/030095, dated May 21, 2012.
International Search Report and Written Opinion for PCT/US2009/066966, dated Jan. 20, 2010.
Third Office Action from related Chinese Patent Application No. 200980150612.6, dated Mar. 31, 2014.
Office Action from related Japanese Patent Application No. 2016-015657, dated Oct. 24, 2016.
International Search Report and Written Opinion for PCT/US2008/086420 dated Mar. 4, 2009.
Fourth Office Action for Chinese Application No. 200980127852.4, dated Jan. 3, 2014.
Fifth Office Action for Chinese Application No. 200980127852.4, dated Jun. 20, 2014.
Appeal Decision for Japanese Patent Application No. 2014-21937 dated Nov. 16, 2015.
First Office Action from related Chinese Application No. 201480012142.8 dated Mar. 27, 2017.
European Patent Office Communication regarding Application No. 09 790 456.9-1528, dated Jun. 8, 2012.
International Search Report and Written Opinion for PCT/US2009/050670 dated Dec. 16, 2009.
Communication pursuant to Article 94(3) from related European Patent Application No. 13174260.3, dated Jun. 30, 2015.
Notice of Reasons for Rejection for Japanese Patent Application No. 2011-518876, dated Oct. 22, 2013.
Communication pursuant to Article 94(3) from related European Patent Application No. 09790456.9, dated May 2, 2013.
Third Office Action for Chinese Patent Application No. 200980127852.4, dated Jul. 25, 2013.
Patent Examination Report No. 1: Australian Patent Application No. 2009270910, dated Dec. 23, 2013.
Fourth Office Action for Chinese Patent Application No. 200980127852.4, dated Jan. 3, 2014.
Fifth Office Action for Chinese Patent Application No. 200980127852.4, dated Jul. 20, 2014.
Office Action from related Chinese Application No. 201280014306.1 dated Mar. 6, 2017.
Official Action from related Mexican Application No. MX/a/2013/010810 dated Feb. 3, 2017.
Official Action from related Mexican Application No. MX/a/2013/010810 dated Jun. 8, 2016.
Office Action from related Russian Application No. 2013145802/14(070849) dated Feb. 26, 2016.
Second Office Action from related Chinese Patent Application No. 201280014306.1 dated Mar. 28, 2016.
Communication pursuant to Article 94(3) from related European Patent Application No. 09771445.5 dated Apr. 4, 2016.
Patent Examination Report No. 2 for related Australian Application No. 2012230845 dated Apr. 6, 2016.
Substantive Examination Report from related Mexican Application No. MX/a/2013/010810 dated Jan. 28, 2016.
Notice of Reasons for Rejection from related Japanese Application No. 2014-501237 dated Jan. 18, 2016.
Appeal Decision for Japanese Patent Application No. 2011-540802 dated Nov. 16, 2015.
First Office Action for related Chinese Patent Application No. 201280014306.1 dated Aug. 3, 2015.
Substantive Examination Report for related Mexican Patent Application No. MX/a/2013/010810 dated Aug. 25, 2015.
European Patent Office Communication from related European Application No. 13745770.1-1654 dated Jan. 3, 2017.

(56) References Cited

OTHER PUBLICATIONS

International Preliminary Report on Patentability for related PCT Application No. PCT/US2013/052419 dated Jan. 27, 2015.
International Preliminary Report on Patentability for related PCT Application No. PCT/US2014/021203 dated Sep. 8, 2015.
International Search Report and Written Opinion for PCT/US2014/021203, dated Jun. 4, 2014.
Office Action from related EPO Application No. 13792797.6-1664 dated Mar. 23, 2017.
International Search Report and Written Opinion for PCT/US2013/067858, dated Feb. 18, 2014.
International Preliminary Report on Patentability for related PCT Application No. PCT/US2013/067858 dated May 5, 2015.
Patent Examination Report No. 2 from Australian Application No. 2010345413 dated Nov. 13, 2015.
Decision of Rejection for Japanese Application No. 2012-537036 dated Nov. 9, 2015.
Official Action for Russian Application No. 2012120588/14(031039) dated Nov. 5, 2014.
Official Action for Russian Application No. 2012120588/14(031039) dated Feb. 25, 2015.
Official Action for Japanese Application No. 2012-537036 dated Apr. 6, 2015.
First Official Action for Chinese Application No. 201080048718.8 dated Apr. 8, 2014.
Notice of Reasons for Rejection for Japanese Application No. 2012-537036 dated Jun. 23, 2014.
International Preliminary Report on Patentability for PCT/US2010/054428 dated May 1, 2012.
International Search Report and Written Opinion for PCT/US2010/054428 dated Apr. 5, 2011.
Japanese Office Action from corresponding International Application No. 2015-561655, dated Jan. 22, 2018.
Chinese Office Action from corresponding International Application No. 201480012142.8, dated Dec. 19, 2017.
Examination Report from corresponding Australian Application No. 2014225705, dated Sep. 1, 2017.
Office Action from corresponding European Application No. 14712951.4, dated Jul. 12, 2017.
Third Office Action from related Chinese Patent Application No. 201480012142.8, dated Jul. 9, 2018.
Office Action from related Russian Patent Application No. 2015142162/14 (065119), dated Feb. 22, 2018 (foreign language only).

* cited by examiner

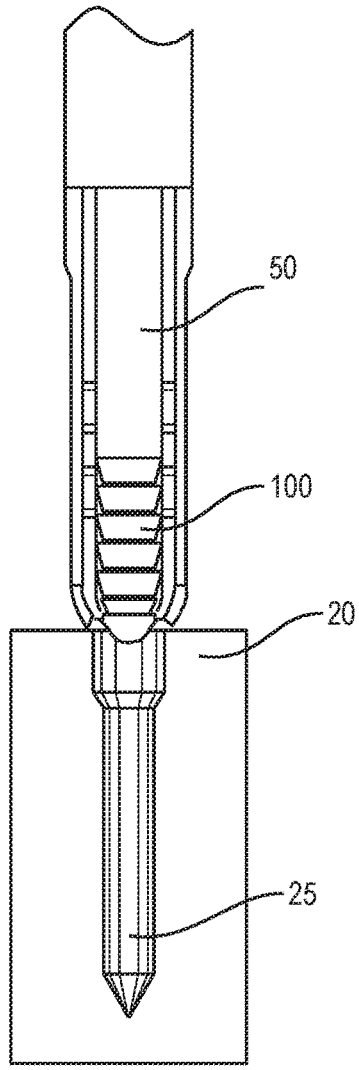
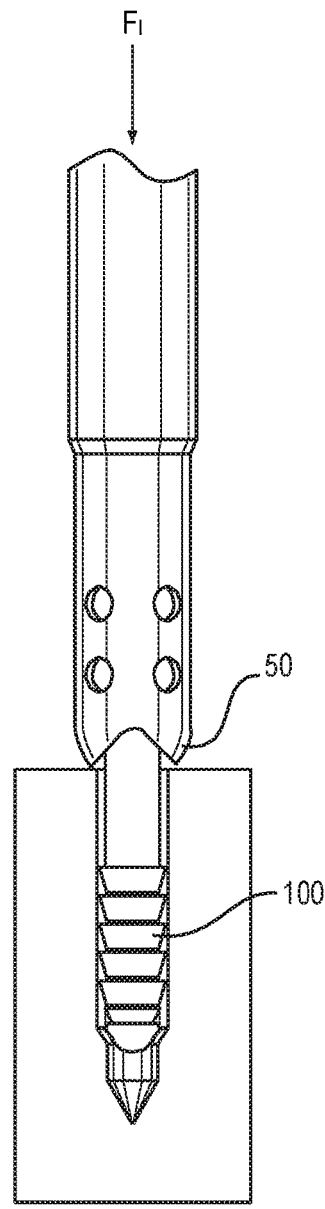
FIG. 2A
FIG. 2B

MICROANCHOR

CROSS-REFERENCE TO RELATED APPLICATION(S)

This application claims the benefit of U.S. Provisional Application No. 61/773,613, filed on Mar. 6, 2013, and entitled, "Microanchor," the entirety of which is hereby incorporated by reference.

BACKGROUND

Surgeons use a variety of suture anchors to conduct soft tissue repair procedures. For these procedures, one or more sutures, called "repair sutures" are attached to a suture anchor, which is or will be fixed to bone. The repair sutures are then used to tie soft tissue down to the bone. There are challenges that arise with prior approaches to joining a repair suture to a suture anchor.

FIG. 1 shows a prior suture-anchor joining approach in which a suture, e.g., repair suture 10, runs externally through a suture channel 12 in the surface of an anchor body and passes through a transverse bore, e.g., eyelet 14. This approach reduces the contact area of anchor ribs against a hole drilled into bone (bone hole or pilot hole), and thus lowers fixation strength. In addition, there is some amount of compression by the surrounding bone on the suture, and into the anchor. This can result in suture damage and difficulty in sliding the repair suture. Suture slide is a function desired when tying knots.

SUMMARY

Described herein are examples of a suture anchor for soft tissue repair that address the foregoing shortcomings and others as well. In one aspect, at least one example described herein provides a suture anchor. The suture anchor includes a body having a proximal end engagable with a suture anchor insertion instrument, a distal end, a longitudinal axis extending between the proximal end and the distal end, and an outer surface extending between the proximal and distal ends. The suture anchor also includes a plurality of projections extending from the surface. The suture anchor also includes a bore extending through the body and transverse to the longitudinal axis. The suture anchor also includes a soft suture bridge comprising a free end through which a repair suture can be fed, the soft suture bridge passing through the bore with the free end extending proximally from the bore.

In another example, the suture anchor may further include one or more of the following, alone or in any combination. The proximal end of the body may include one of a protrusion or recess for engaging a complementary recess or protrusion, respectively, of a suture anchor insertion instrument. The distal end of the body may terminate at a distal tip configured for inserting into a hole prepared in bone. Alternatively, the distal end of the body may terminate at a distal tip configured for inserting into bone without a hole prepared in the bone. The projections may include a plurality of annular ribs or a plurality of wings. The free end may include a first free end and a second free end, each having a preformed eyelet sized to receive the repair suture which permits the repair suture to slide. In some examples, the preformed eyelets are located in the region of the proximal end of the body. In other examples, the preformed eyelets are located proximal to the proximal end of the body. The soft suture bridge may be a suture and the free end of the suture is pierced, in use, by the repair suture. A pair of channels may be formed in the surface of the body and extend proximally from the bore. The plurality of projections may include one of a plurality of partial ribs or a plurality of wings between the pair of channels. A recess may be defined at the proximal end and orientated traverse to the longitudinal axis. The recess may have a cross section larger than a cross section of the repair suture which permits the repair suture to slide. The pair of channels extends between from the bore and recess. At least one fenestration may be formed in the body for facilitating bone ingrowth. The bore extending through the body may comprise a first bore and a second bore located proximal to the first bore. A body may comprise a bridge located between the first bore and the second bore, and a cannulation extending, proximally, from the second bore and along the longitudinal axis. The soft suture bridge may extend around the bridge and through the cannulation towards the proximal end of the body. A repair suture may be fed through the free end of the soft suture bridge. The body may have a diameter between 1 mm and 3 mm. The body may comprises a material selected from a formulation of poly(lactic-co-glycolic) acid (PLGA), β-Tricalcium phosphate (β-TCP) and calcium sulfate, poly-L-lactic acid-hydroxyapatite (PLLA-HA), polyether ether ketone (PEEK) or variants thereof. The distal end of the body may terminate in a tip comprising a metal selected from titanium, stainless steel or variants thereof.

In one aspect, at least one example described herein provides a suture anchor installation system. The system includes a suture anchor installation instrument. The suture anchor installation instrument includes a handle and a shaft extending from the handle. The suture anchor installation instrument also includes an inserter tip extending from the shaft and terminating at a distal terminal end. The system also includes any suture anchor with a soft suture bridge described herein disposed that the distal terminal end of the suture anchor installation instrument.

In another example, the suture anchor installation system may further include one or more of the following, alone or in any combination. The inserter tip having a longitudinal axis may include a recess extending, proximally, from the distal terminal end towards the handle and along the longitudinal axis. The proximal end of the body may include a protrusion that is complementary to the recess of the suture anchor insertion instrument. The inserter tip may include a passageway extending through the inserter tip and transverse to the longitudinal axis. The passageway is configured to permit the repair suture to be routed, externally, along the outside of the inserter tip and the shaft.

In one aspect, at least one example described herein provides a method for repairing soft tissue. The method includes providing any suture anchor with a soft suture bridge described herein. The method also includes inserting the suture anchor, distal end first, into bone. The method also includes sliding the repair suture through the soft suture bridge to tie a knot in the repair suture and attach soft tissue to the bone.

In another example, the method for repairing soft tissue may further include one or more of the following, alone or in any combination. The method may include drilling a hole into the bone and inserting the suture anchor into the hole. The method may include repositioning the soft tissue by sliding the repair suture through the soft suture bridge.

In one aspect, at least one example described herein provides a cannulated suture anchor. The cannulated suture anchor includes an anchor body having a distal end and a proximal end engagable with a suture anchor insertion instrument. The cannulated suture anchor also includes a soft suture bridge disposed at the proximal end of the anchor body, through which a repair suture is fed and freely slidable in a soft tissue repair procedure. The anchor body defines a cannulation, extending between the proximal and distal ends of the anchor body, through which a suture forming the soft suture bridge passes. The suture has a knot securing the soft suture bridge at the distal end of the anchor body. In some examples of the cannulated suture anchor, the knot securing the soft suture bridge at the distal end of the anchor body is an overmolded, crimped or heat stiffened knot. In other examples of the cannulated suture the knot securing the soft suture bridge at the distal end of the anchor body and a portion of the suture forming the soft suture bridge is an overmolded, crimped or heat stiffened assembly.

In one aspect, at least one example described herein provides a suture anchor with an insert-molded soft suture bridge.

In one aspect, at least one example described herein provides a method for tying a knot at one end of a soft suture bridge of a suture anchor for soft tissue repair. The method includes passing a needle internally through the woven structure of a suture. The needle being passed a distance (first passage length) that determines the size and strength of the knot. The method also includes pulling the suture through itself leaving a short length before a loop, and leaving a long length of suture after the loop. The method also includes placing the long length of the suture back through the loop created. The method also includes multiplying the desired suture eyelet length by two to determine a length. The method also includes measuring the determined length from the location where the suture is first run through itself to locate a point. The method also includes, at the point located, passing a needle internally through the woven structure of a suture, the needle being passed another distance (second passage length) that further determines the size and strength of the knot. The method also includes, tightening both loops of the knot to form a suture eyelet. The method also includes pulling the suture eyelet through a cannulated suture anchor used for soft tissue repair procedure.

BRIEF DESCRIPTION OF THE DRAWINGS

The accompanying drawings, which are incorporated in and form a part of the specification, illustrate examples of the present disclosure and together with the written description serve to explain the principles, characteristics, and features of the disclosure. In the drawings:

FIGS. 2A-2C are side views on a suture anchor with a soft suture bridge being inserted into bone.

DESCRIPTION

In the following detailed description of the illustrated examples, reference is made to accompanying drawings, which form a part thereof, and within which are shown by way of illustration, specific examples, by which the subject matter can be practiced. It is to be understood that other examples can be utilized and structural changes can be made without departing from the scope of the disclosure.

The particulars shown herein are by way of example and for purposes of illustrative discussion of the examples only and are presented in the case of providing what is believed to be the most useful and readily understood description of the principles and conceptual aspects of the disclosure. In this regard, no attempt is made to show structural details of the subject matter in more detail than is necessary for the fundamental understanding of the disclosure, the description taken with the drawings making apparent to those skilled in that how the several forms of the present disclosure can be embodied in practice. Further, like reference numbers and designations in the various drawings indicate like elements.

Figure 1:
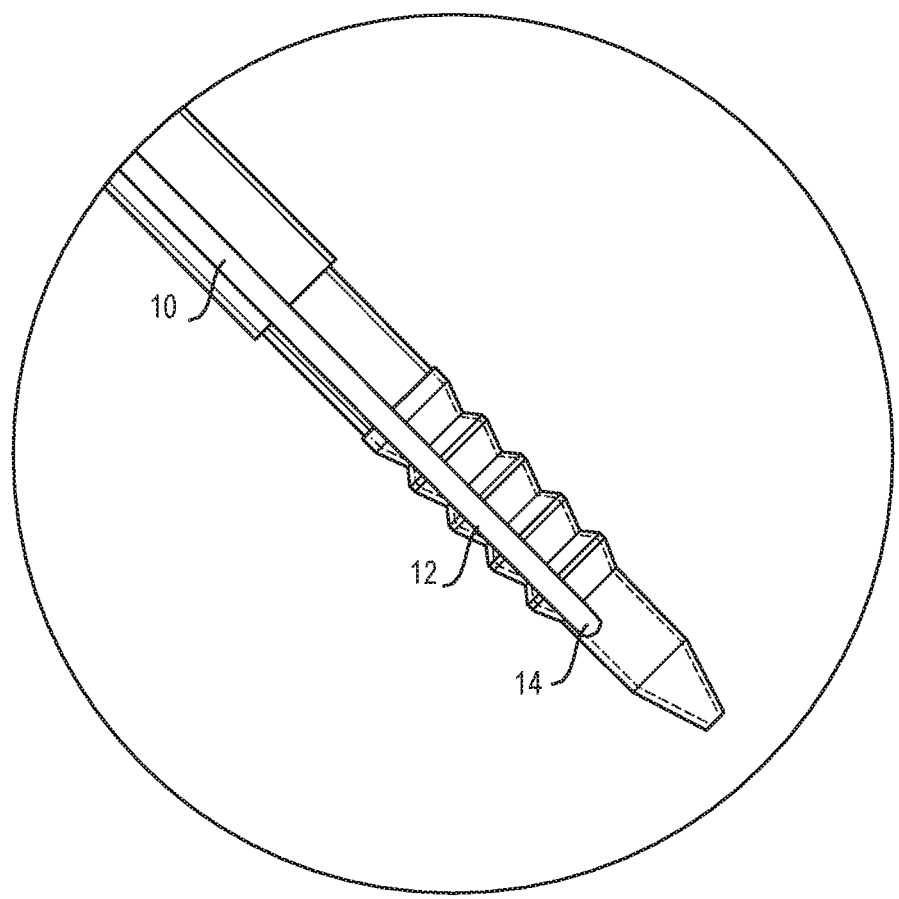
FIG. 1 is a view of a suture anchor using a prior suture-anchor joining approach.
Figure 2C:
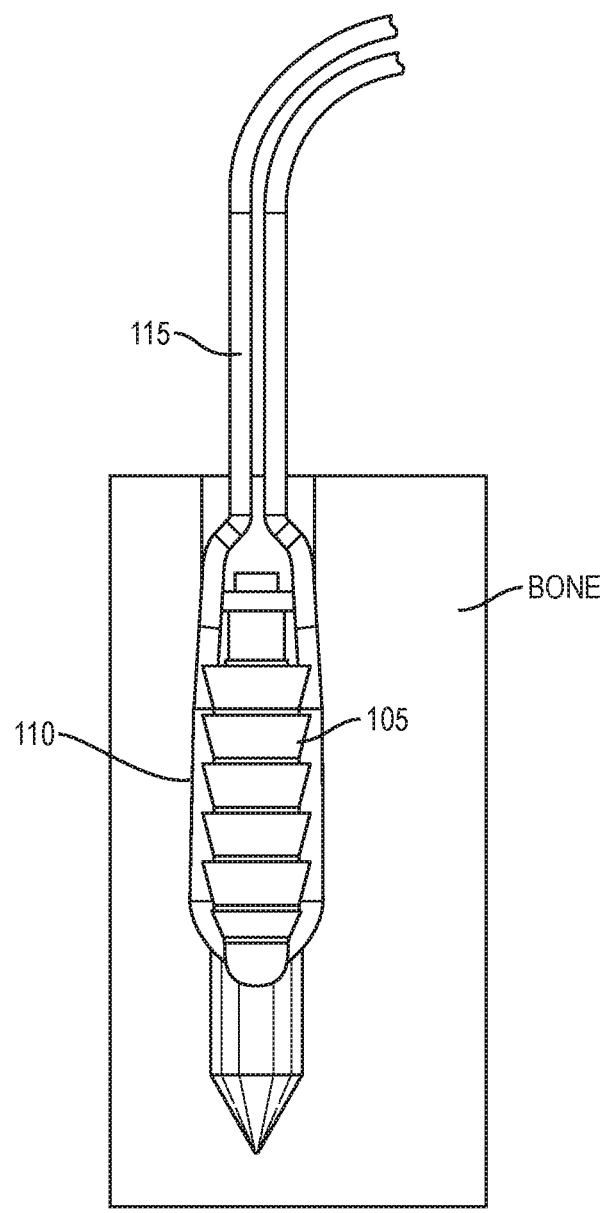

FIGS. 2A-2C show an example suture anchor 100 being inserted into bone. As more clearly shown in FIG. 2C, the suture anchor 100 includes a body 105, soft suture bridge 110 coupled to the body 105, and a repair suture 115 fed through the soft suture bridge 110. The suture anchor 100 is at an end of a suture anchor insertion instrument. As shown in FIG. 2A, a surgeon uses the suture anchor insertion instrument 50 to insert the suture anchor 100, distal end first, into a hole prepared in bone 20 or "bone hole" 25. As shown in FIG. 2B, the surgeon pushes on suture anchor insertion instrument or hits it with a mallet (shown as an insertion force $F_I$) to push the suture anchor 100 into the hole. The suture anchor 100 moves into the hole until the desired insertion depth is reached, as shown in FIG. 2C. The desired insertion depth may be controlled, for example, by a positive stop feature between a drill guide and the suture anchor insertion instrument, or when a mark on the suture anchor insertion instrument matches up with a respective line on a drill guide.

The surgeon uses the repair suture 115 to attach soft tissue to the bone. More specifically, the surgeon passes one or more limbs of the repair suture 115 through the soft tissue and ties one or more knots in the repair suture 115, securing the soft tissue to the bone. As the surgeon ties the knots, the repair suture 115 slides with respect to the soft suture bridge 110. The ability for the repair suture 115 to slide, referred to as "suture slide," is beneficial because it allows the surgeon to tie knots in the repair suture 115 and secure the soft tissue to the bone. Suture slide further allows the surgeon to position and reposition the soft tissue, readily.

Figure 3A:
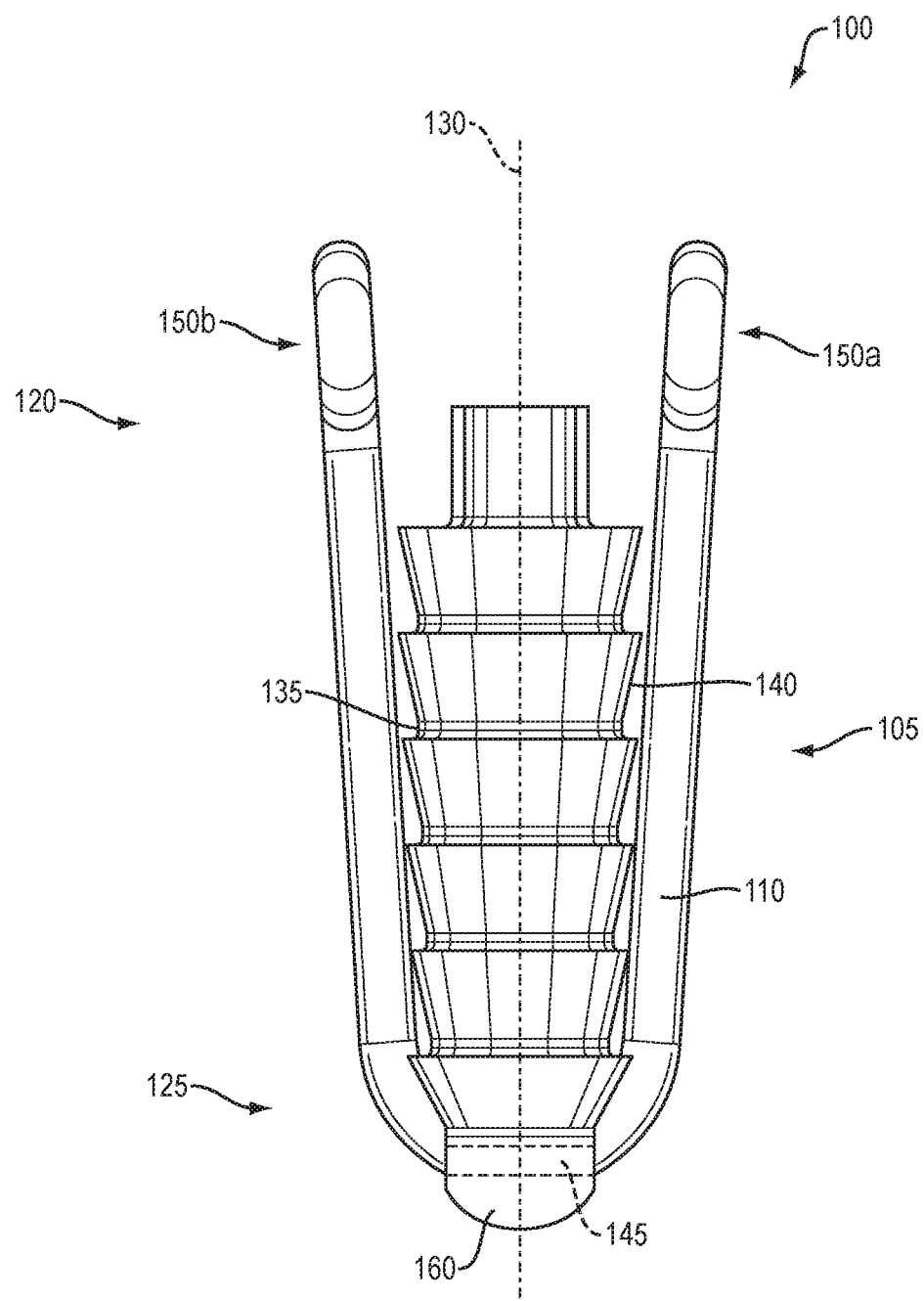
FIGS. 3A and 3B are views of an example of the suture anchor with soft suture bridge.
Figure 3B:
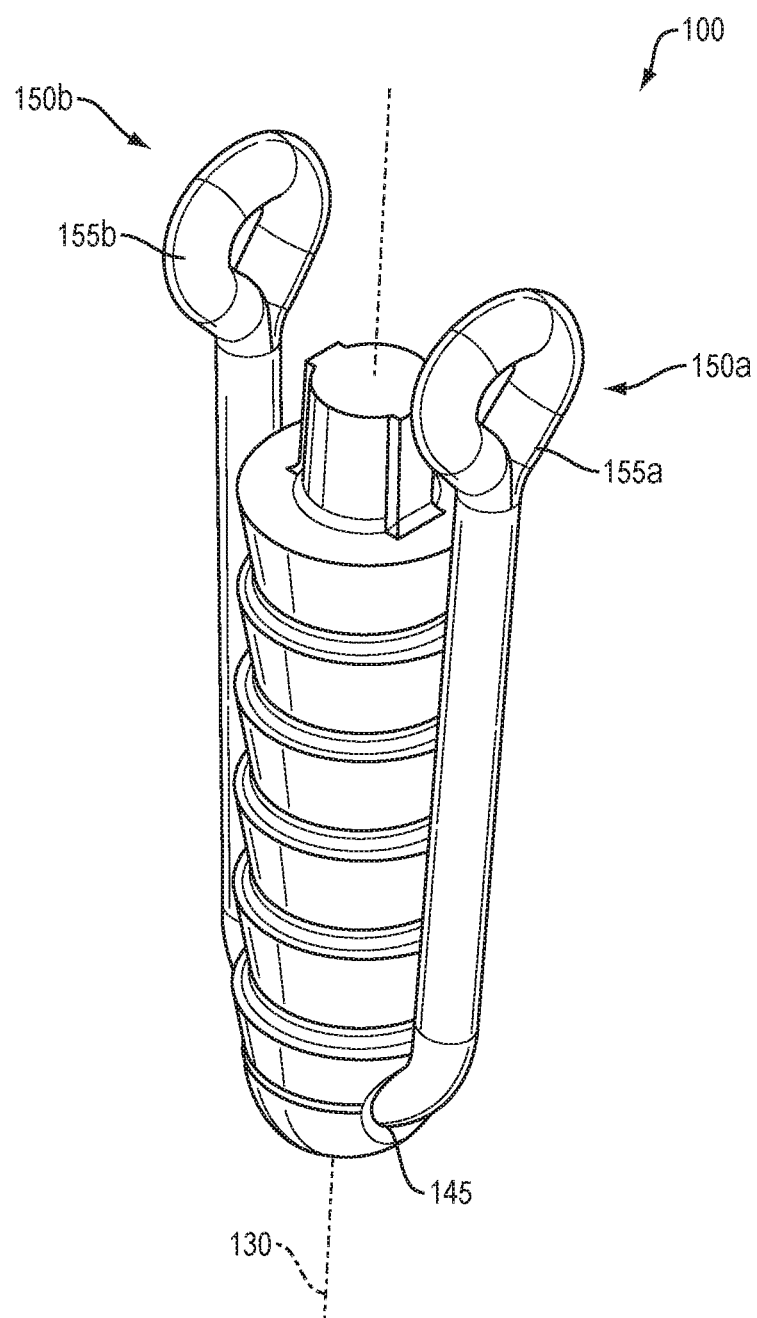

FIGS. 3A and 3B show an example of the suture anchor 100. The body 105 has a proximal end 120, distal end 125, and longitudinal axis 130 extending between the proximal and distal ends 120, 125. A surface 135 extends between the proximal end 120 and distal end 125 along the longitudinal axis 130. A plurality of annular ribs 140 extend from the surface 135. When the suture anchor 100 is inserted into the bone, the plurality of annular ribs 140 provides an interference fit and secures the suture anchor 100 to the bone. As more clearly shown in FIG. 3B, at the distal end 125, there is a bore 145 extending through the body 105 and transverse to the longitudinal axis 130. The soft suture bridge 110 extends from the transverse bore 145.

In some examples, the soft suture bridge 110 is a length of suture or suture tape. In other examples the soft suture bridge 110 is a molded part. In each of these examples, the soft suture bridge 110 includes at least one free end 150 (e.g., 150a). The free end 150 extends proximally from the bore 145. The repair suture 115 can be fed through the free end 150. In one example in which the soft suture bridge 110 is a length of suture, the soft suture bridge 110 is, in use, pierced, interlaced or otherwise interwoven by the repair suture 115.

As shown, a convenient example of the soft suture bridge 110 has a first free end 150a and second free end 150b. As best seen in FIG. 3B, each of the free ends 150a,b includes a preformed eyelet 155a,b (generally 155). The preformed eyelet 155 is sized to receive the repair suture 115 which permits the repair suture 115 to slide. In one example, the preformed eyelet 155 defines an aperture sized 0% to 30% larger than the cross-section of the repair suture 115.

In another example of the preformed eyelet 155, the size of the aperture is 0% to 30% smaller than the cross-section of the repair suture 115. The periphery of the preformed eyelet 155 that defines the undersized aperture or the entire eyelet itself is made from a resilient material, for example. As the surgeon pulls the repair suture 115 through the preformed eyelet 155, the resilient material enables the undersized aperture to increase in size and thereby permits the repair suture 115 to slide. When the surgeon stops pulling the repair suture 115, the undersized aperture returns to its original size and thereby inhibits the repair suture 115 for sliding.

As shown, a convenient configuration of the soft suture bridge 110 has the preformed eyelets 155 with a circular aperture that complements the circular cross-section of the repair suture 115. It should be readily apparent that other examples of the preformed eyelet 155 may have apertures triangular, square, or oval in shape, just to name a few. As further shown, the preformed eyelets 155 are located proximal to the proximal end 120 of the body 105. This location of the preformed eyelets 155 permits easy movement of the repair suture 115.

The distal end 125 of the body 105 terminates at a distal tip 160. In some examples, the distal tip 160 is integral with the body 105 or the distal tip 160 is constructed separately and affixed to the body 105. The distal tip 160 can be constructed of any suitable material, including for example, metal (e.g., surgical stainless steel, titanium or variants thereof), polymer (e.g., polyether ether ketone (PEEK)), composite (e.g., carbon fiber PEEK), or bioabsorbable materials. Other commonly used material for implants are also contemplated by this disclosure.

In various examples, the distal tip 160 can be designed with the appropriate strength, stiffness, and shape (e.g., a pointed, conical, metal tip) for penetrating the hard outer cortical layer of bone without the need for a hole, referred to as a "no-hole-prep" tip. This configuration of the distal tip 160 is particularly advantageous because it eliminates the step of drilling a hole. Consequently, a surgeon can insert a no-hole-prep example of the suture anchor 100 in less time than a conventional screw-in anchor. The surgeon can also install more of the no-hole-prep suture anchors in a given period of time. As such, some examples of the suture anchor 100 can advantageously shorten surgery time.

However, it will be apparent in view of this disclosure that, in accordance with various examples, the distal tip 160 can be designed to be inserted into a bone after a hole is provided in the bone. For example, the distal tip 160 may have the general shape of a truncated cone, which is easier to install into the bone hole, particularly one that is undersized. Such examples of the distal tip 160 are beneficial, particularly, when the distal tip 160 is constructed from brittle bioabsorbable or osteoconductive materials.

As shown, the plurality of annular ribs 140 are formed circumferentially around the body 105 and stacked along at least part of a longitudinal length of the body 105. In various examples, the annular ribs 140 are stacked along the entire longitudinal length of the body 105. However, it will be apparent in view of this disclosure that, in accordance with various examples, the annular ribs 140 are stacked along only a portion of the longitudinal length of the body. The cross-sectional shape of each annular rib, in accordance with various examples, can include triangular, square, rectangular, trapezoidal, polygonal, circular, or any other suitable cross-sectional shape.

The geometry of the annular ribs 140 is selected based on the ability to be inserted into a bone hole and the ability to be retained in a bone hole. For example, a convenient example of the annular ribs 140 taper from a first rib diameter at a proximal portion of the body 105 to a smaller, second rib diameter at a distal portion of the body 105, as shown. The taper may, in examples, reduce the force required to insert the suture anchor 100 into bone, reducing the risk of unwanted bone damage. Where a bone hole is desirable, in accordance with various examples, the diameter of at least one of the annular ribs 140 is sized for compressive fitting in a predetermined diameter of the bone hole.

Figure 4A:
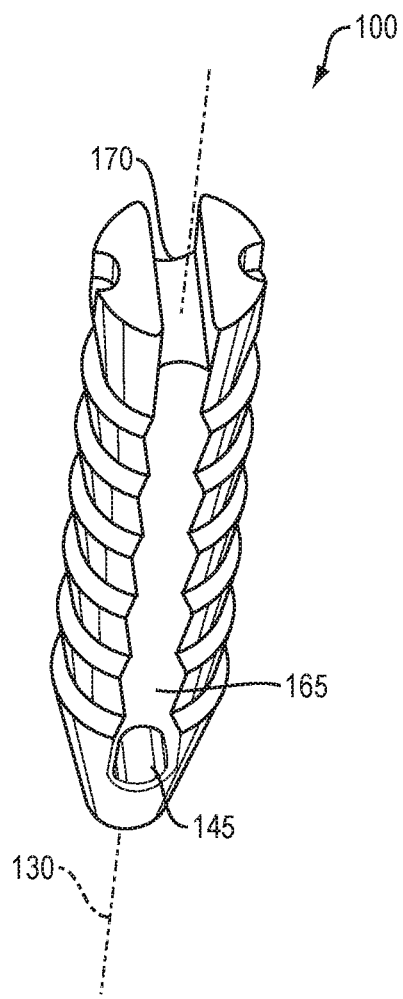
FIGS. 4A and 4B are views of another example of the suture anchor with soft suture bridge.
Figure 4B:
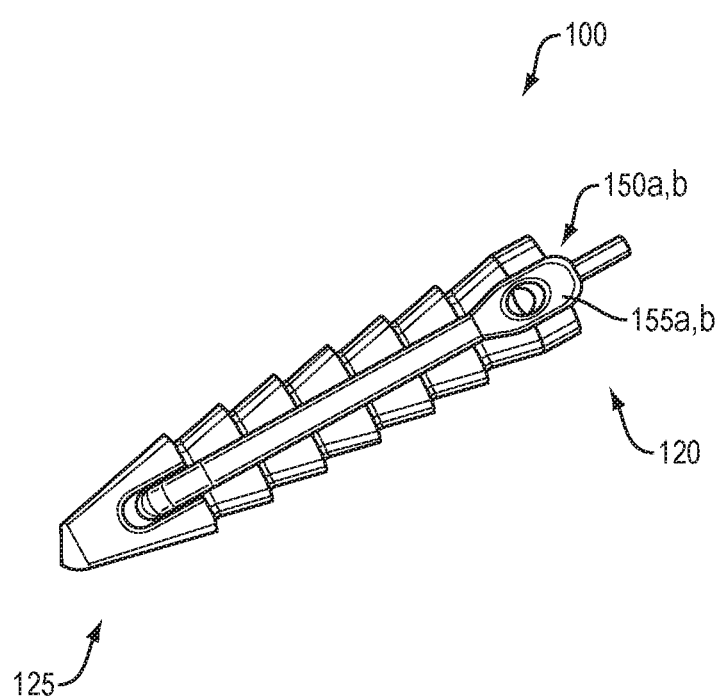

FIGS. 4A and 4B show another example of the suture anchor 100 with channels 165. The channels 165 are formed in the surface 135 of the body 105. The channels 165 are configured to receive portions of the soft suture bridge 110. The channels 165 extend, proximally, from the transverse bore 145 through at least a portion of the surface 135 of the body 105. Generally, the channels 165 are opposing one another. In accordance with various examples, a depth of the channels 165 can be constant or vary along a longitudinal length of each channel 165. In a convenient example, the depth of the channels 165 is selected such that a portion of the soft suture bridge 110, which is received in the channels 165, lies beyond the plurality of annular ribs 140. In this configuration, portions of soft suture bridge 110 are compressed between the channels 165 and bone contributing to the overall interference fit of the suture anchor 100.

As more clearly shown in FIG. 4B, the proximal end 120 of the body 105 includes a recess 170. The recess 170 is orientated traverse to the longitudinal axis 130. The channels 165 extend between the transverse bore 145 and recess 170. The recess 170 has a cross-section larger than a cross-section of the repair suture 115 which permits the repair suture 115 to slide through the recess 170. In this configuration, the first and second free ends 150a,b of the soft suture bridge 110 are at the proximal end 120 of the body 105 and are aligned with the recess 170. The repair suture 115 is routed in through the first free end 150a, through the recess 170, and out through the second free end 150b.

As shown, the first and second free ends 150a,b of the soft suture bridge 110 include preformed eyelets 155a,b formed in flattened sections of the soft suture bridge 110. In other examples, the preformed eyelets 155a,b are shaped as shown and described above with reference to FIGS. 3A and 3B. While the example shown in FIGS. 4A and 4B includes both the channels 165 and recess 170, other examples of the suture anchor 100 include the channels 165 or the recess 170.

Figure 5A:
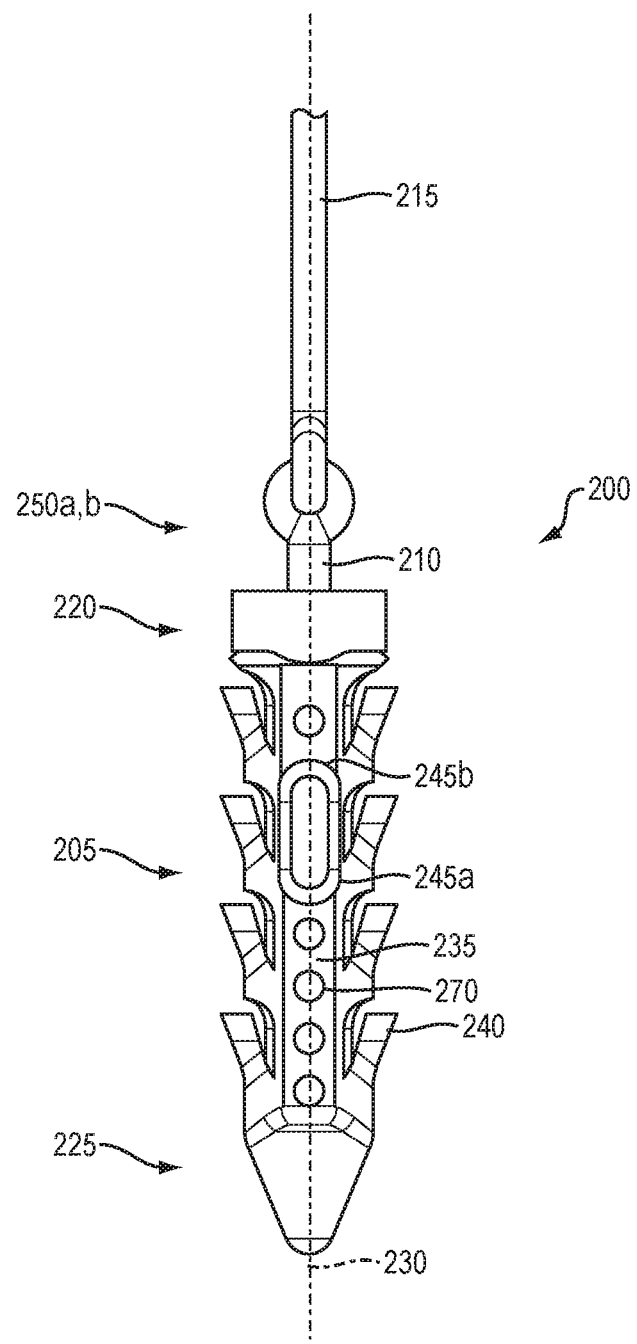
FIGS. 5A-5C are views of a fenestrated suture anchor with a soft suture bridge.
Figure 5B:
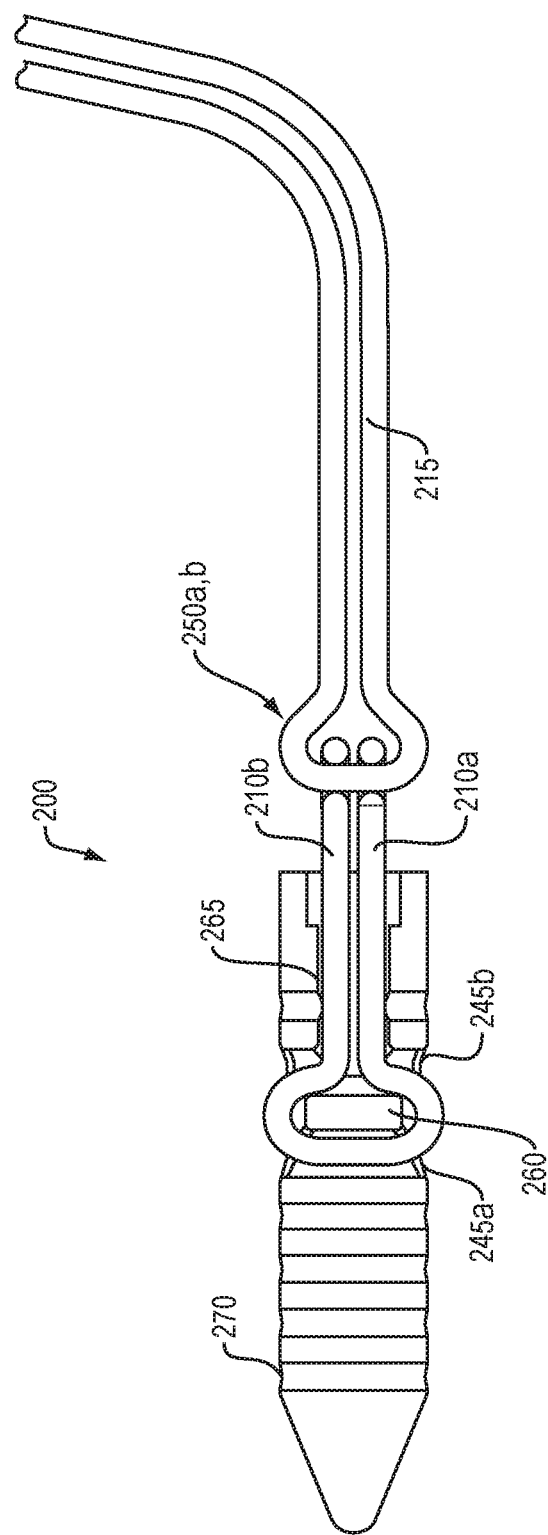

FIGS. 5A and 5B show a fenestrated suture anchor 200 including a body 205, a soft suture bridge 210 coupled to the body 205, and a repair suture 215 feed through the soft suture bridge 210. The body 205 has a proximal end 220, distal end 225, and longitudinal axis 230 extending between the proximal and distal ends 220, 225. A surface 235 extends between the proximal and distal ends 220, 225 along the longitudinal axis 230. Examples of the soft suture bridge 210 are described above with reference FIGS. 3A, 3B, 4A, and 4B. Free ends 250a,b of the soft suture bridge 210 extend, proximately, beyond the proximal end 220 of the body 205. The repair suture 215 can be fed through the free ends 250a,b.

As more clearly seen in FIG. 5B, the fenestrated suture anchor 200 includes fenestrations 270 defined by the surface 235 and formed through the body 205. The fenestrations 270 provide a way for bone to grow into the fenestrated suture anchor 200. This bone ingrowth is desirable because it contributes to the success of the soft tissue repair and promotes natural healing. The number, size, and/or arrangement (e.g., spacing and distribution) of the fenestrations 270 are selected to facilitate bone ingrowth. In making this selection, further consideration is given to maintaining suitable compressive strength needed to insert the fenestrated suture anchor 200 into bone, particularly, into an under-sized bone hole or into bone directly for "no-hole prep" installation. While the fenestrations 270 are shown as passageways extending entirely through the body 205, other examples, such as dimples, holes that do not extend entirely through the anchor body, and other means for allowing boney ingrowth, are also contemplated.

The fenestrated suture anchor 200 further includes a plurality of wings 240 extending from the surface 235. When the fenestrated suture anchor 200 is inserted into bone, the plurality of wings 240 provides an interference fit and secures the fenestrated suture anchor 200 to the bone. As shown, the plurality wings 240 are grouped into two rows, each diametrically opposed to one another. Other examples include more than two rows of wings (e.g., 3 or 4 rows) radially arranged about the body. The structure of an individual wing making up the plurality wings 240 is described in more detail below.

Between adjacent rows of wings, the fenestrated suture anchor 200 includes a first bore 245a and a second bore 245b located proximal to the first bore 245a. As more clearly seen in FIG. 5B, a bridge 260 separates the first bore 245a and second bore 245b. A cannulation 265 defined by the body 205 extends proximately from the second bore 245b. The cannulation 265 is sized to receive the soft suture bridge 210. For example, as shown the cannulation 265 has a diameter that accommodates "doubled over" 210a portions of the soft suture bridge 210.

The soft suture bridge 210 extends around the bridge 260 and through the cannulation 265 towards the proximal end 220 of the body 205. As shown, in a convenient example of the suture anchor 200, portions 210b of the soft suture bridge 210 projecting from the first bore 245a and second bore 245b extend beyond the surface 235 of the body 205. When the suture anchor 200 is installed in bone, these portions 210b of the soft suture bridge 210 are compressed between the bridge 260 and bone. Advantageously, this suture routing arrangement contributes to overall interference fit of the suture anchor.

Figure 5C:
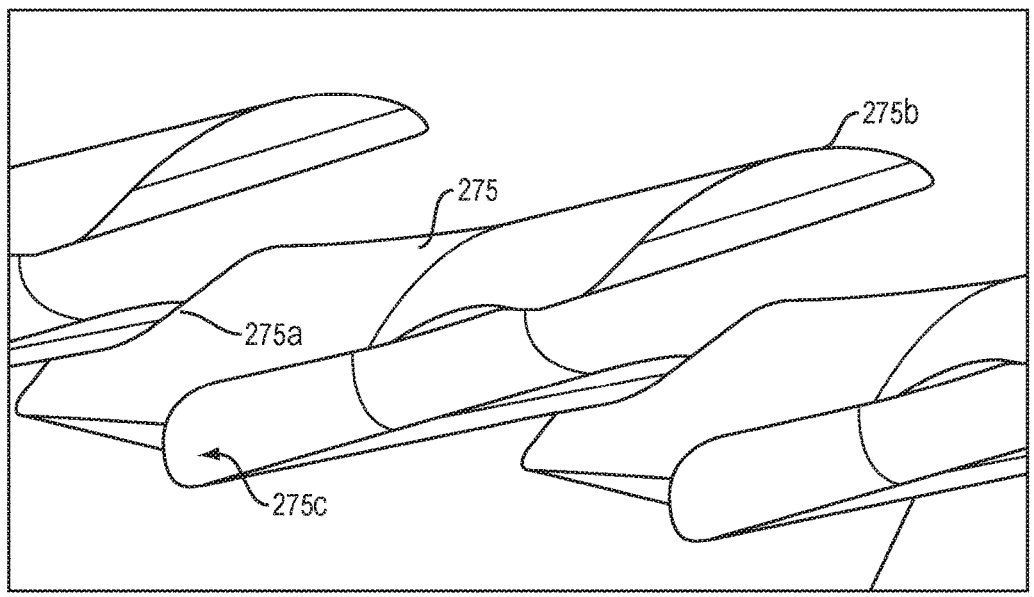

With reference to FIG. 5C, a wing 275 includes a base 275a and a wing tip 275b. The wing 275 extends outwardly from the base 275a, at an angle to the surface 235 of the body 205, towards the proximal end 220 of the body 205. The angle is selected so that the wing 275 flexes inwardly with the wing tip 275b moving towards the surface 235 of the body 205 in response to an insertion force. The wing 275 flexes outwardly with the wing tip 275b moving away from the surface 235 of the body 205 in response to a pull out force.

The wing 275 further includes, at the base 275a, a clearance 275c. The dimensions of the clearance 275c (e.g., length, width, and radius) are selected to provide the wing 275 with suitable flexibility. The wing 275 further has a profile defined between the base 275a and wing tip 275b. The profile is selected to provide sufficient resistance to being pulled out. For example, as shown, the profile of the wing 275 flares outwardly near the wing tip 275b. This flared profile is designed to catch the hard outer cortical layer when the fenestrated suture anchor 200 is withdrawn from bone. Accordingly, such a profile is advantageous to achieving high fixation strength of the fenestrated suture anchor 200.

Figure 6A:
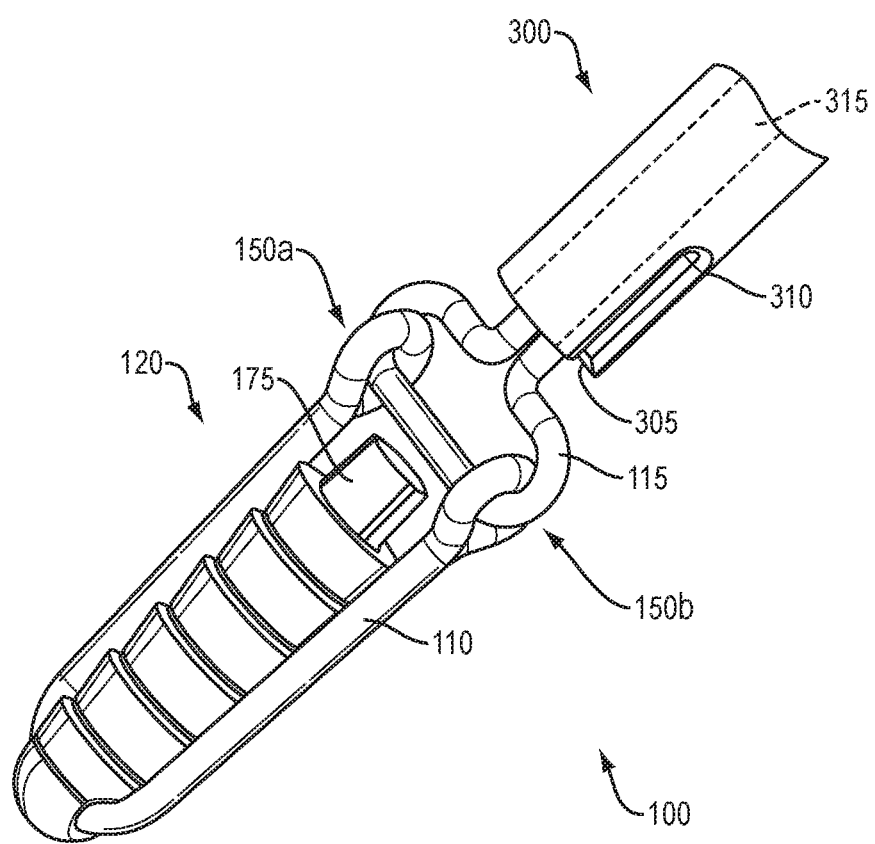
FIGS. 6A-6B are views of an inserter tip of a suture anchor insertion instrument used to insert examples of the suture anchor into bone.
Figure 6B:
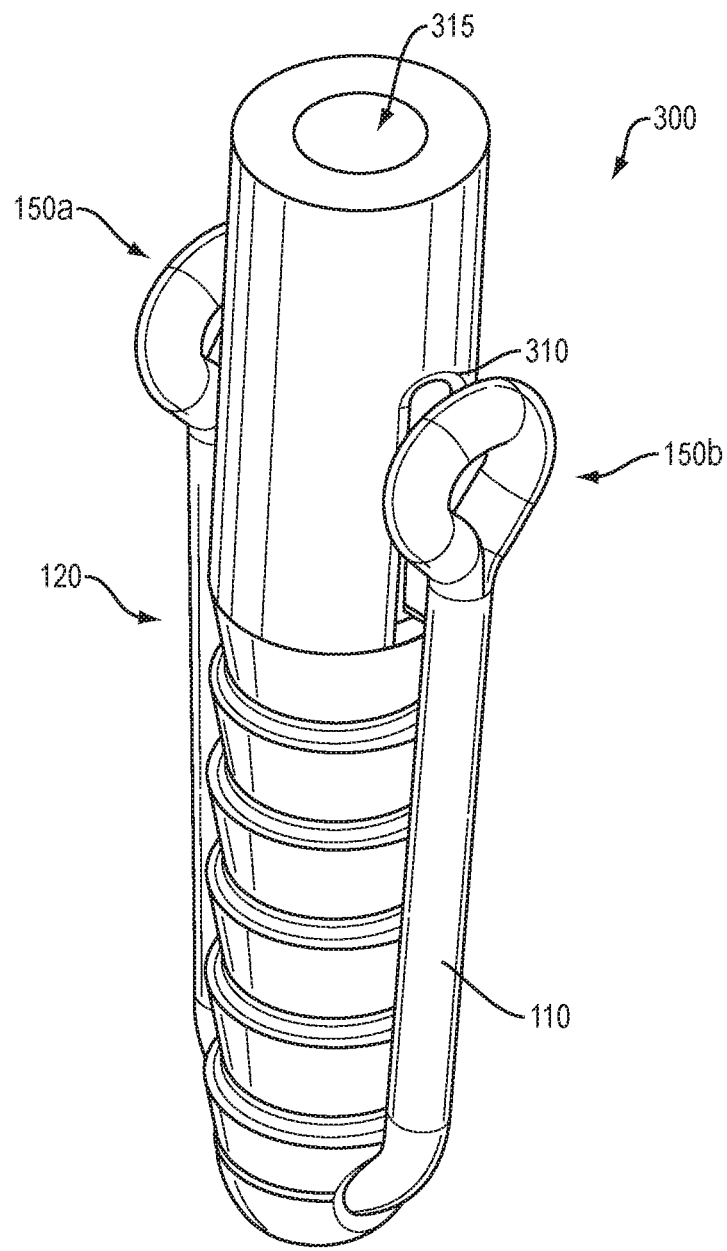

FIGS. 6A and 6B show an inserter tip 300 of a suture anchor insertion instrument used to insert examples of the suture anchor 100 of FIGS. 3A and 3B. As more clearly shown in FIG. 6A, the suture anchor 100 includes a protrusion 175 at the proximal end 120 of the body 105. The inserter tip 300 includes a complementary recess 305 for engaging the protrusion 175. The protrusion 175 and recess 305 are shown having a circular cross-sectional shape. Other examples can be constructed with a cross-sectional shape including triangular, hexagonal, polygonal and cross-shaped, to name a few. In still other examples, the protrusion 175 includes projections that are engagable with complementary grooves or recesses in the inner surface/wall of the recess 305, or vice versa, for a bayonet-type fit.

The insertion tip 300 includes a passageway 310 for accommodating the repair suture 115, which has been fed through the soft suture bridge 110. As more clearly shown in FIG. 6B, when the suture anchor 100 is coupled to the inserter tip 300, the free ends 150a,b of the soft suture bridge 110 are at either side of the inserter tip 300. The inserter tip 300 is an extension of a shaft (not shown), which ultimately terminates with a handle (not shown). Some examples of the handle include one or more suture-holding grooves or knobs formed into the handle for holding the repair suture 115.

To insert examples of the suture anchor 200 of FIG. 5A-5C, an insertion tip similar to the insertion tip 300, described above. may be used. The insertion tip has a geometry for mating with the proximal end of the suture anchor 200. The insertion tip and the suture anchor insertion instrument associated with it may also include some of the features described above with reference to FIGS. 6A and 6B.

Figure 7:
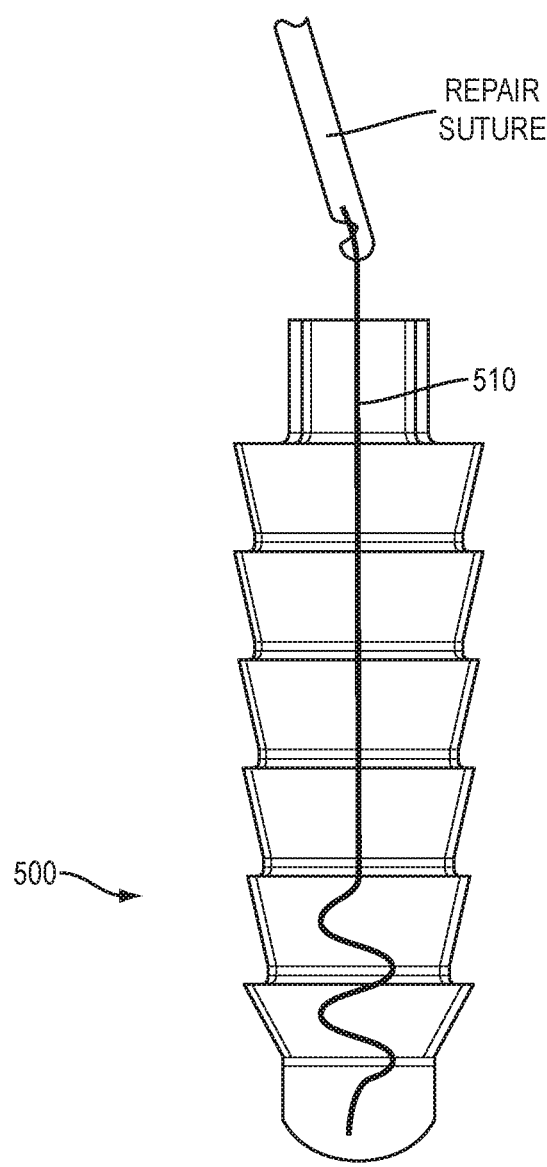
FIG. 7 is a side view of an example suture anchor with a soft suture bridge molded into the body of the suture anchor.

FIG. 7 shows example of a suture anchor 500 having one or more sutures (e.g., a single strand suture) insert-molded to form a soft suture bridge 510 at a proximal end of the suture anchor 400. In this example, the suture is placed in a suture anchor mold prior to (injection) molding the suture anchor 500.

Figure 8:
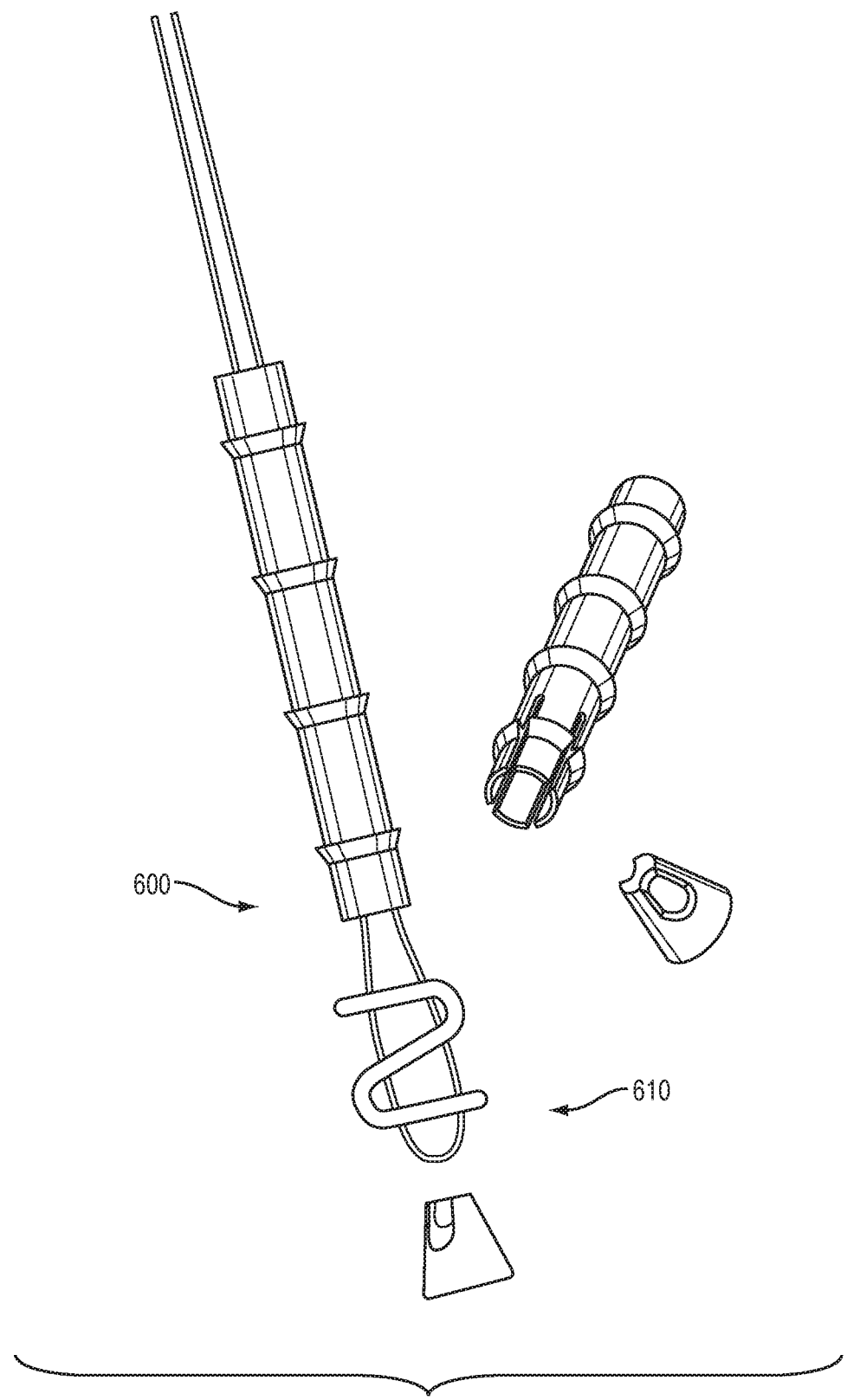
FIG. 8 includes views of an example suture anchor with a distal soft suture bridge.

While the foregoing examples of a soft suture bridge are described as being at a proximal end of a suture anchor (e.g., the soft suture bridge 110 of FIGS. 2A-2C), FIG. 8 shows a suture anchor 600 having a soft suture bridge 610 at a distal end of the suture anchor 600. One example of the suture anchor 600 includes a body and conical tip. The body has a distal end with slots. Moving the conical tip into the distal end of the body expands the distal end, radially. This expansion produces an interference fit between the suture anchor 600 and a bone hole and secures the suture anchor 600 to the bone. Another example of the suture anchor 600 includes an expendable knot instead of the conical tip. Moving the expendable knot into the distal end and actuating the expendable knot causes the distal end to expand and creates an interference fit. In addition to being a way of expanding the suture anchor 600, radially, the expendable knot serves as a pulley for a repair suture. Examples of the expanding knot include a suture construct that bunches up when pulled.

FIGS. 9A-F show a cannulated suture anchor 400 and its examples. The cannulated suture anchor 400 includes a body 405, a soft suture bridge 410 coupled to the body 405, and a repair suture 415 feed through the soft suture bridge 410. The body 405 has a proximal end 420, distal end 425, and longitudinal axis 430 extending between the proximal and distal ends 420, 425. A surface 435 extends between the proximal and distal ends 420, 425 along the longitudinal axis 430. A plurality of annular ribs 440 extend from the surface 435. Examples of the plurality of annular ribs 440 are described above with reference FIGS. 3A and 3B.

The cannulated suture anchor 400 and its examples, encompass a unique approach of suture passage that protects the soft suture bridge 410 and facilitates repair suture slide. As more clearly seen in FIG. 9B, the cannulated suture anchor 400 includes a cannulation 445 (or lumen or axial through bore), extending between proximal and distal ends 420, 425 of the body 405. Portions 410a of the soft suture bridge 410 pass through cannulation 470. For ease of reference, this "internal" soft suture bridge is called a "suture eyelet" 410. This arrangement maximizes the contact area of the suture anchor with the bone, resulting in better fixation strength of the suture anchor. Another advantage of this arrangement is that it protects the suture eyelet 410 from damage upon insertion of the suture anchor into the bone.

Figure 9A:
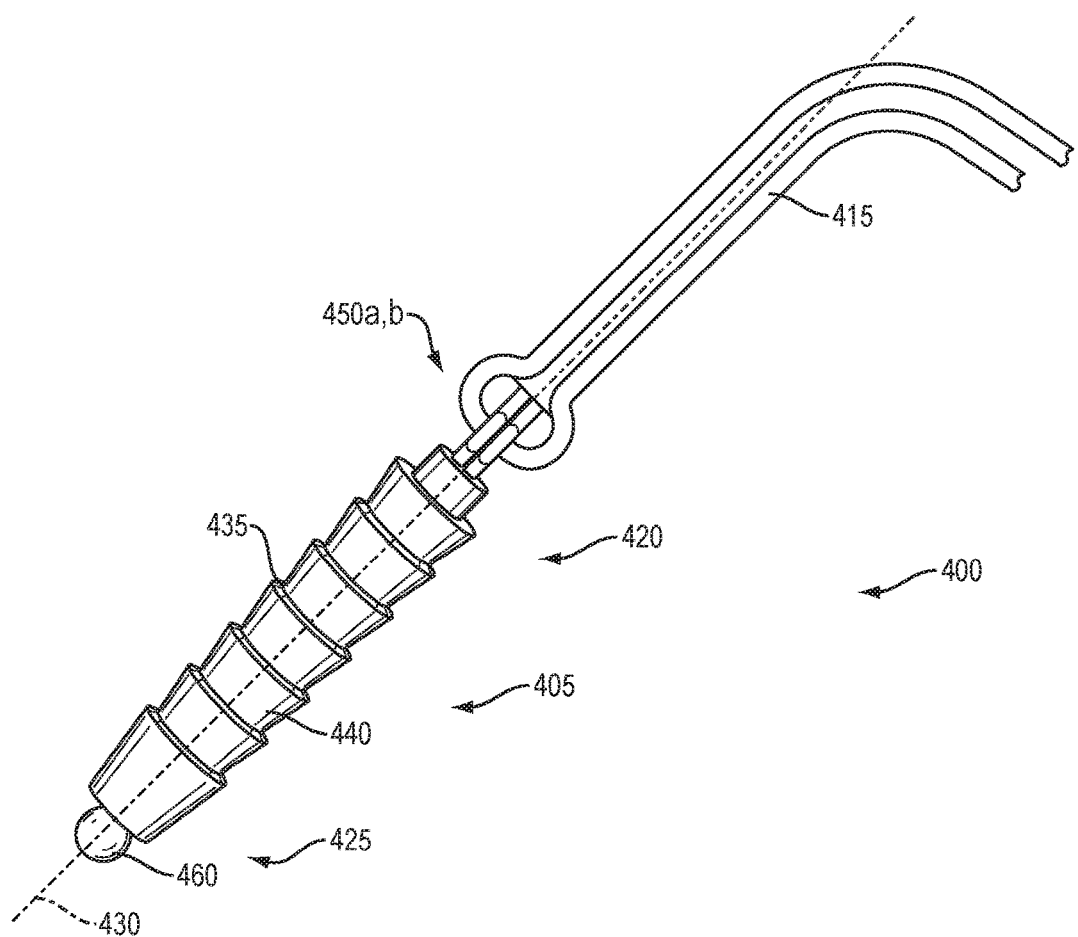
FIGS. 9A-9G are views of a cannulated suture anchor with a suture eyelet and its examples.
Figure 9B:
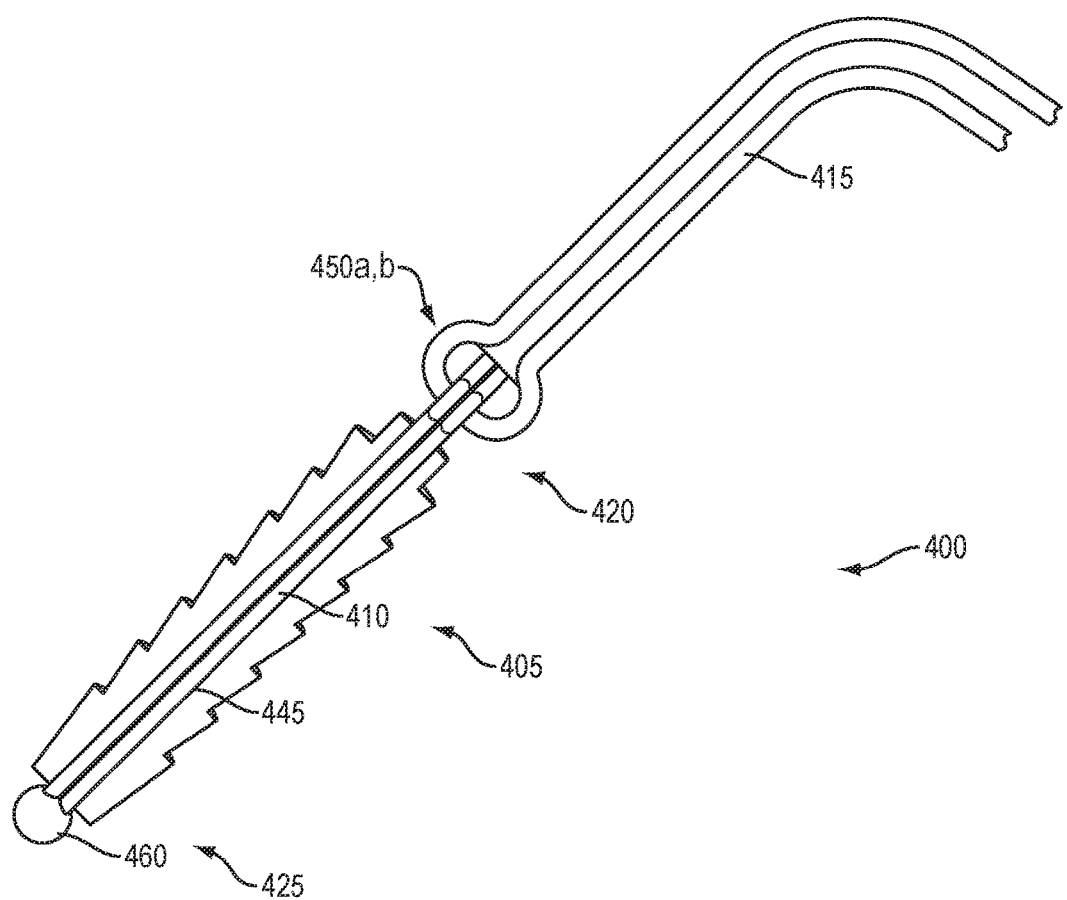
Figure 9C:
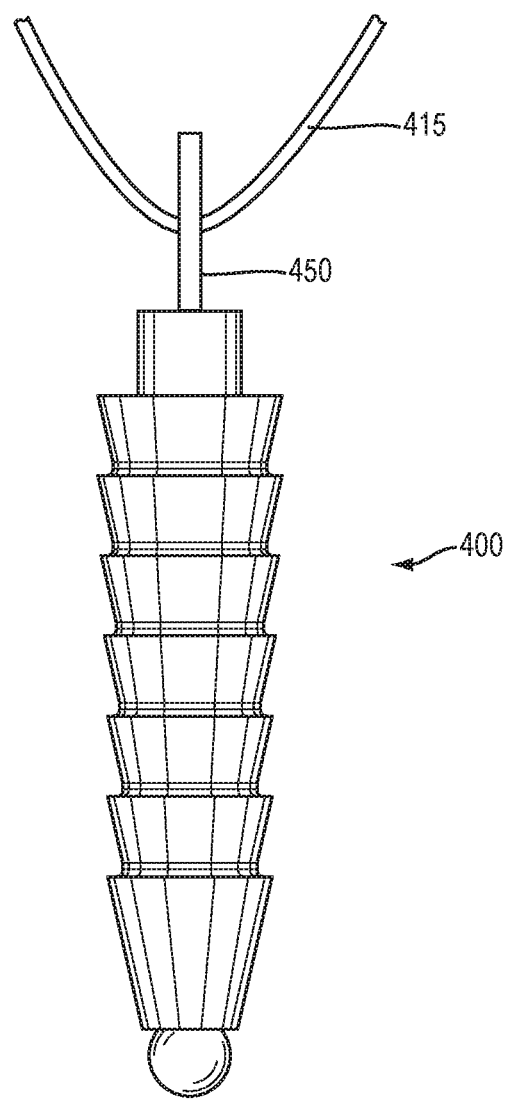
Figure 9D:
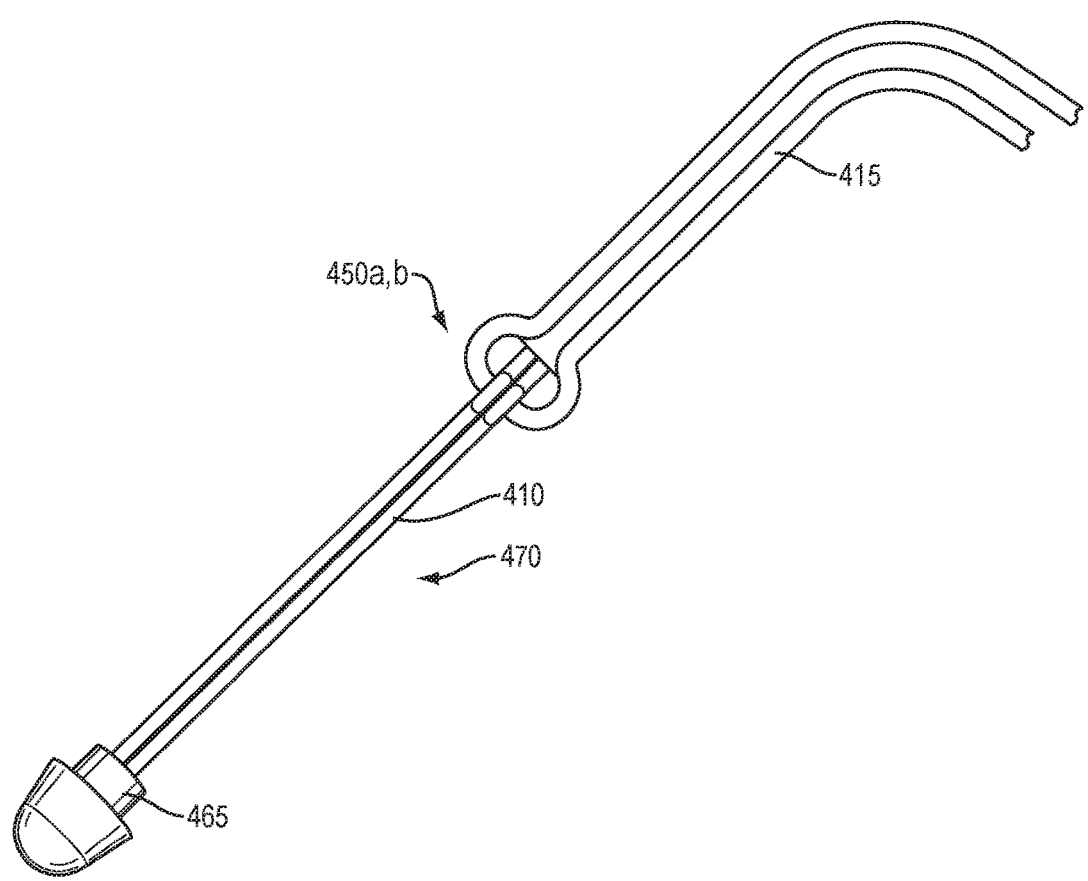
Figure 9E:
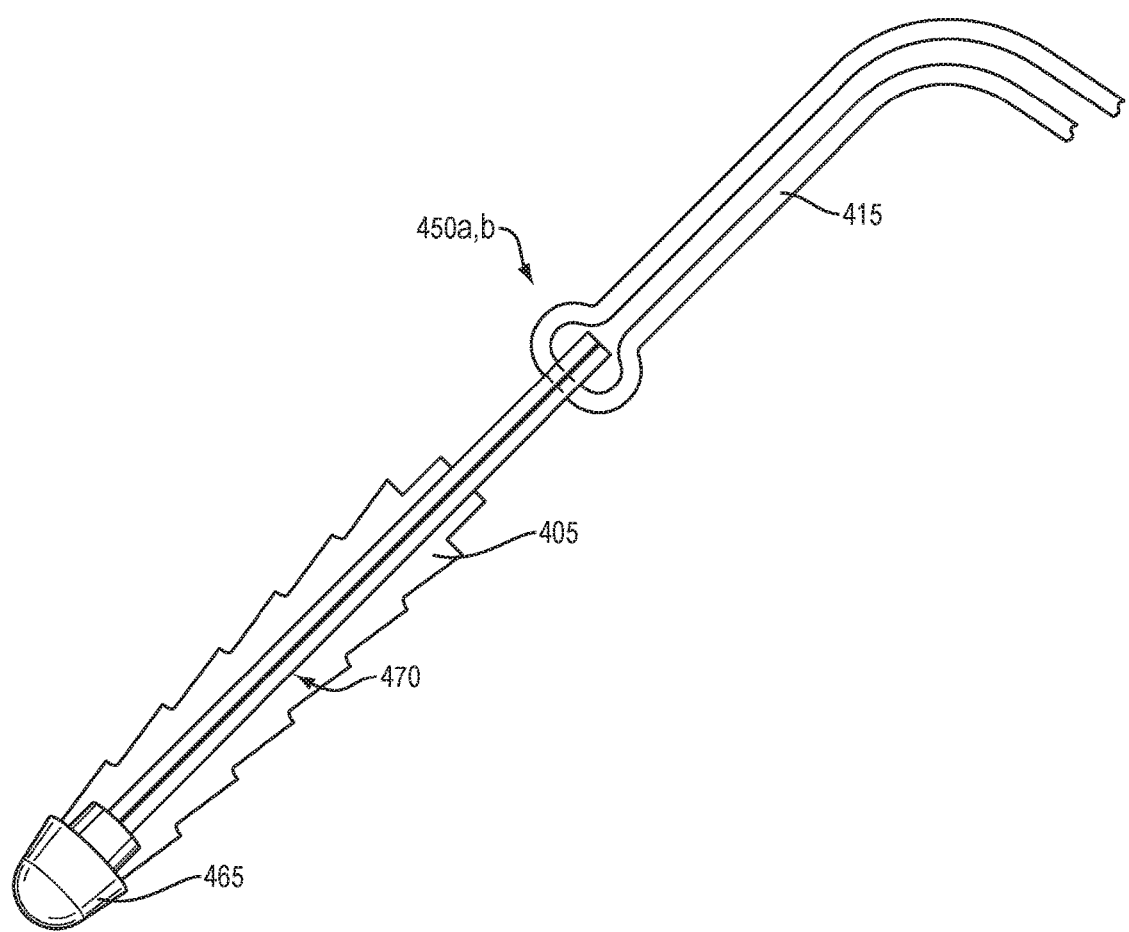
Figure 9F:
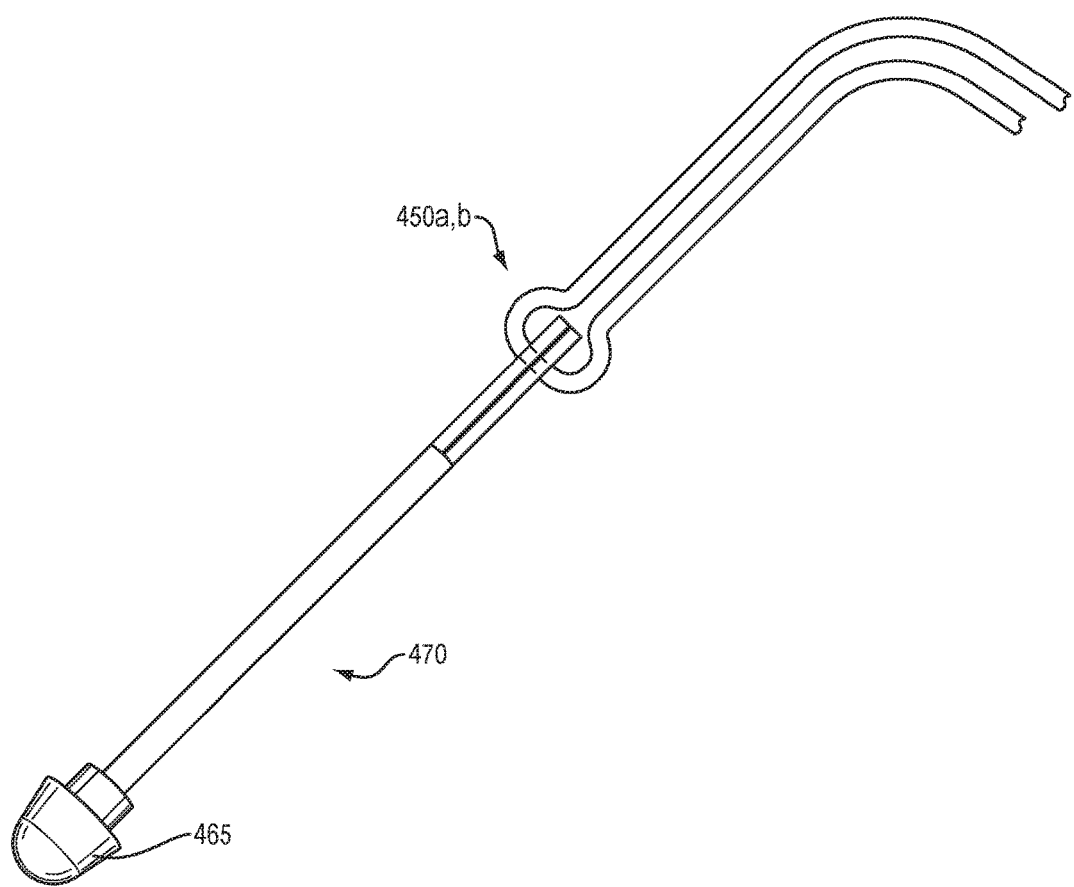
Figure 9G:
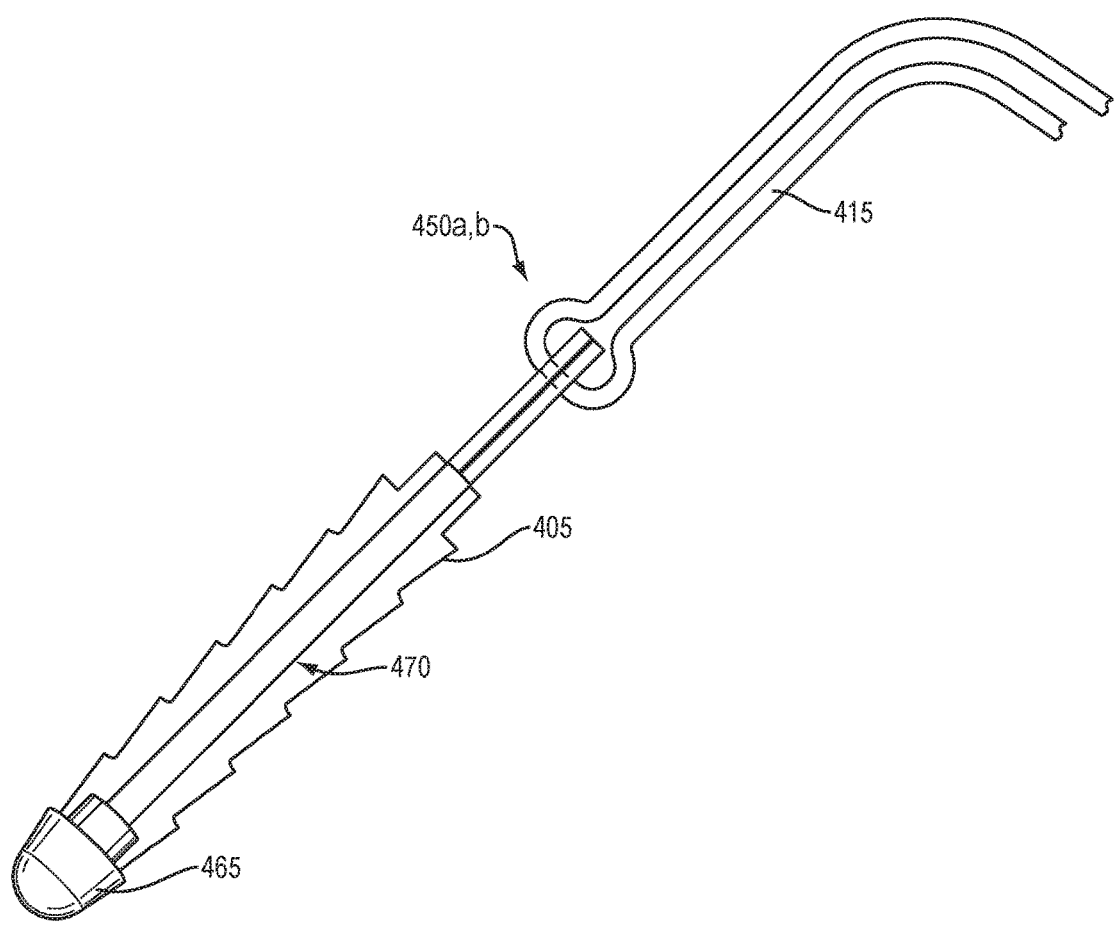

As shown, two free ends 450a,b of the suture eyelet 410 extend, proximately, beyond the proximal end 420 of the body 405. The repair suture 415 can be fed through the two free ends 450a,b. This arrangement is advantageous because it allows for easy movement of the repair suture 415 through the suture eyelet 410. While a convenient example of the suture eyelet 410 is described above as having two free ends, other examples can have one free end, as shown in FIG. 9C.

A knot 410 at a distal end of the suture eyelet 410 is slightly bigger in size than the inner diameter of the body 405. The knot 410 keeps the suture eyelet 410 from pulling through the body 405. In FIGS. 9A-9C, the knot 410 is represented as a sphere for visualization purposes. The actual geometry of the knot 410 may vary. The knot 410 and an example method for tying knot 410 are described in greater detail below.

FIGS. 9D-9G show other examples of the cannulated suture anchor 400 that makes us of a mechanically structured knot 465 at the distal end of the suture eyelet 410. This construct of suture eyelet 410 and mechanically structured knot 465 is referred to as a "structured suture eyelet" 470. Advantageously, the structured suture eyelet 470 can be a rigid body thereby increasing the likelihood of successful off-axis, non-flush, and dense bone insertion of the cannulated suture anchor 400. This is especially true in the example of the cannulated suture anchor 400 shown in FIGS. 9F and 9G, in which almost the entire length of the structured suture eyelet 470 is overmolded (shown in the figure as a sleeve-like structure).

The mechanically structured knot 465 mates with the body 405 of the cannulated suture anchor 400. In a convenient example, the mechanically structured knot 465 includes a protrusion that fits into a complementary recess in the body 405. Advantageously, this permits for flush mating geometry between the body 405 and suture eyelet 415 minimizing the possibility of damaging bone during installation of the cannulated suture anchor 400.

The mechanically structured knot 465 can be achieved through manufacturing techniques, such as overmolding, or mechanical techniques, such as heat stiffening or crimping. The mechanically structured knot 465 allows for a more secured suture eyelet 410 that reduces (and sometimes eliminates) the possibility of knot damage both in use of the cannulated suture anchor 400 and in the manufacturing of the cannulated suture anchor 400. Because the knot is mechanically structured, another advantage includes less variation in the distal knot geometry.

Other examples include different mold geometries for the suture anchor and structured suture eyelet. How the suture anchor and structured suture eyelet mate together can vary. In addition, the method by which the knot at the distal end of suture eyelet ("distal suture eyelet knot") is formed can be a number of ways (molding, crimping, and heat stiffening).

Turning now to a description of a knot used to tie a suture eyelet (such as the suture eyelet 410 described above with reference to FIGS. 9A-9C) called a "Suture Eyelet Knot." The Suture Eyelet Knot is tied through and upon itself, in a manner that prevents the Suture Eyelet Knot from coming undone. The Suture Eyelet Knot and its examples can be used to solve a variety of challenges encountered in tissue repair. In many cases, an example of the Suture Eyelet Knot once tied cannot come undone.

Relevant to the medical field, surgeons require the use of anchors in order to perform soft tissue repair procedures. A repair suture is used to tie down soft tissue back to bone. In some cannulated anchors, it is favorable to run a suture eyelet (or soft suture bridge) through the inner diameter of an anchor. The suture eyelet is tied with the use of a knot that can be subject to a variety of tying methods. Certain knots, however, may come undone due to cyclic loading or high tension impulse forces. The foregoing makes other knots less predictable.

In the past, different types of knots were used, some of which were not tied onto and through themselves as is Suture Eyelet Knot and its examples. In some cases, the issue of knot tying is avoided. For example, the need for a knot can be eliminated by running a suture around or through the anchor. Other methods of fixation include clamping, bonding, etc. Some anchors work around the issue of knot tying by either overmolding a suture into an anchor, or accepting the risk of pull out with a different form of knot.

A method of tying the Suture Eyelet Knot and its examples is described below.

Figure 10A:
FIGS. 10A-G is a series of views of tying a suture eyelet knot.

With reference to FIG. 10A, step 1, start by passing a needle internally through the woven suture of a suture for approximately 1 mm (passage length varies depending on desired knot size and strength). The needle should come out on the same side as it went in. For clarification, this means that the needle does not pierce in one side and out the other. The needle is passed internally through the hollow threads, which are woven in a circumferential manner.

The suture should loop around and upon itself. Specifically, the end of suture which the sharp tip of the needle is facing, should be run so that it first passes through the needle hole end that was initially pierced, and then out the other end.

Figure 10B:
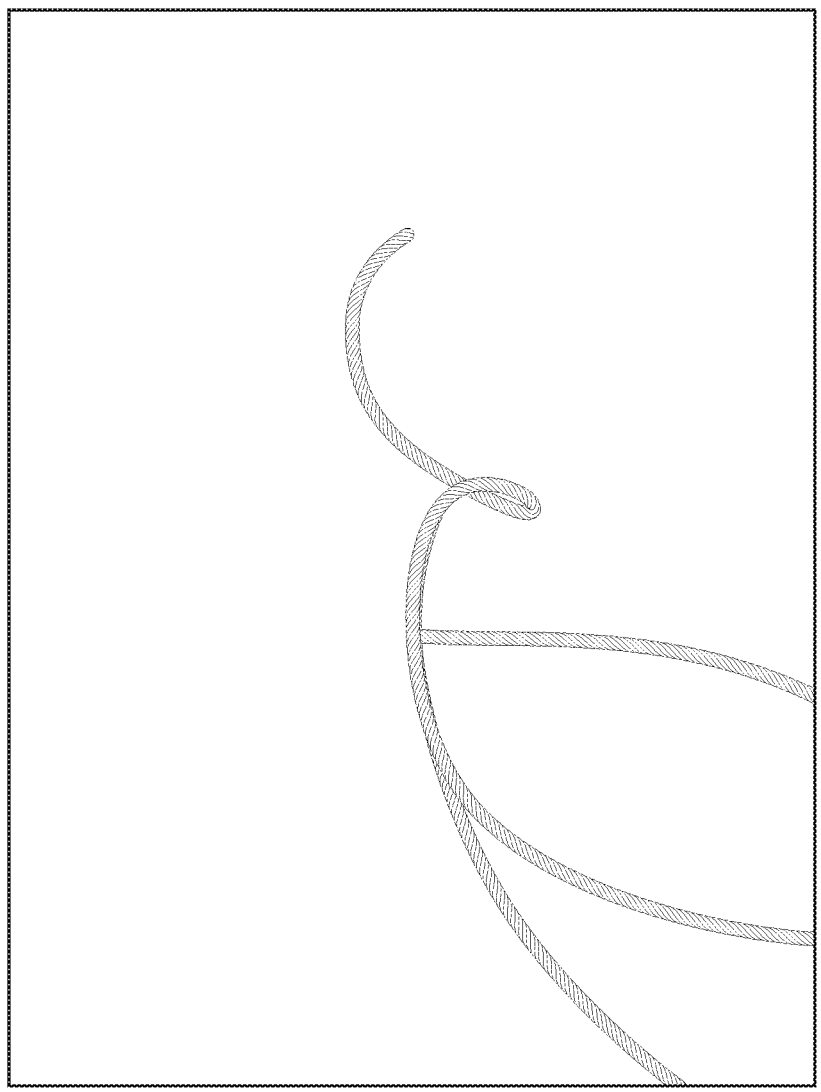

With reference to FIG. 10B, step 2, pull the suture through itself leaving a short length before the loop, and a long length of suture after the loop.

Figure 10C:
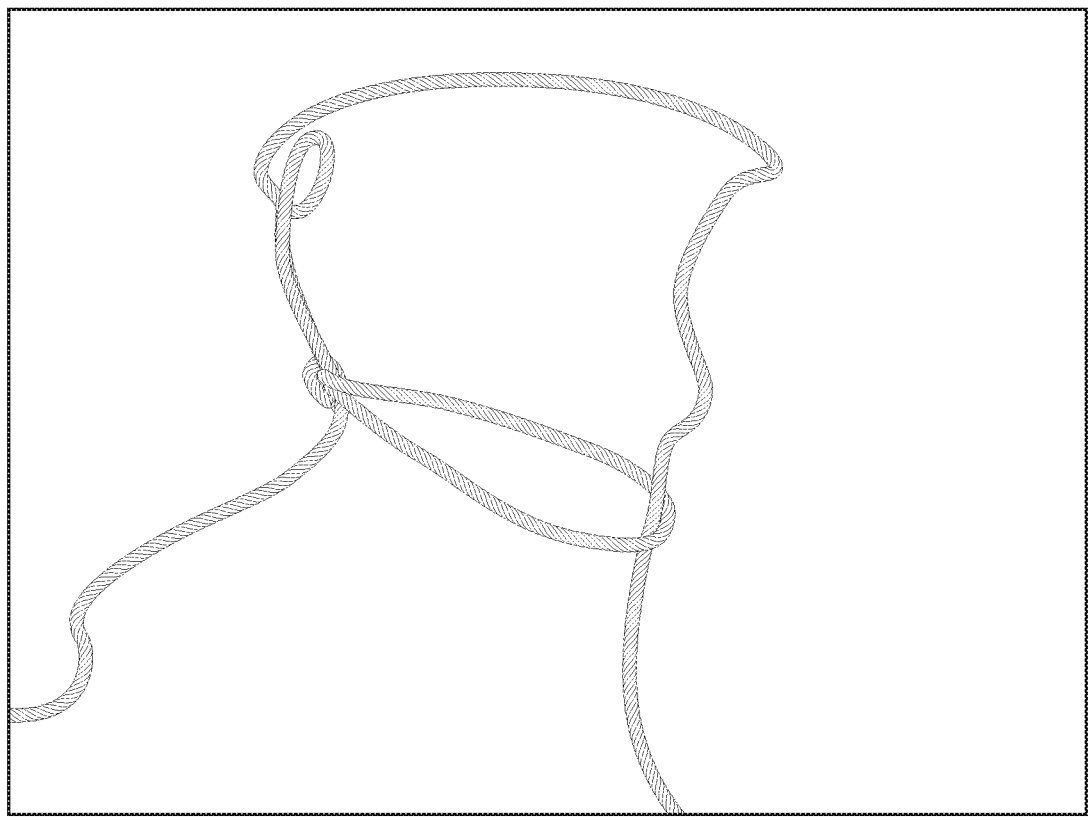

With reference to FIG. 10C, step 3, place the long end of the suture back through the loop created.

Figure 10D:
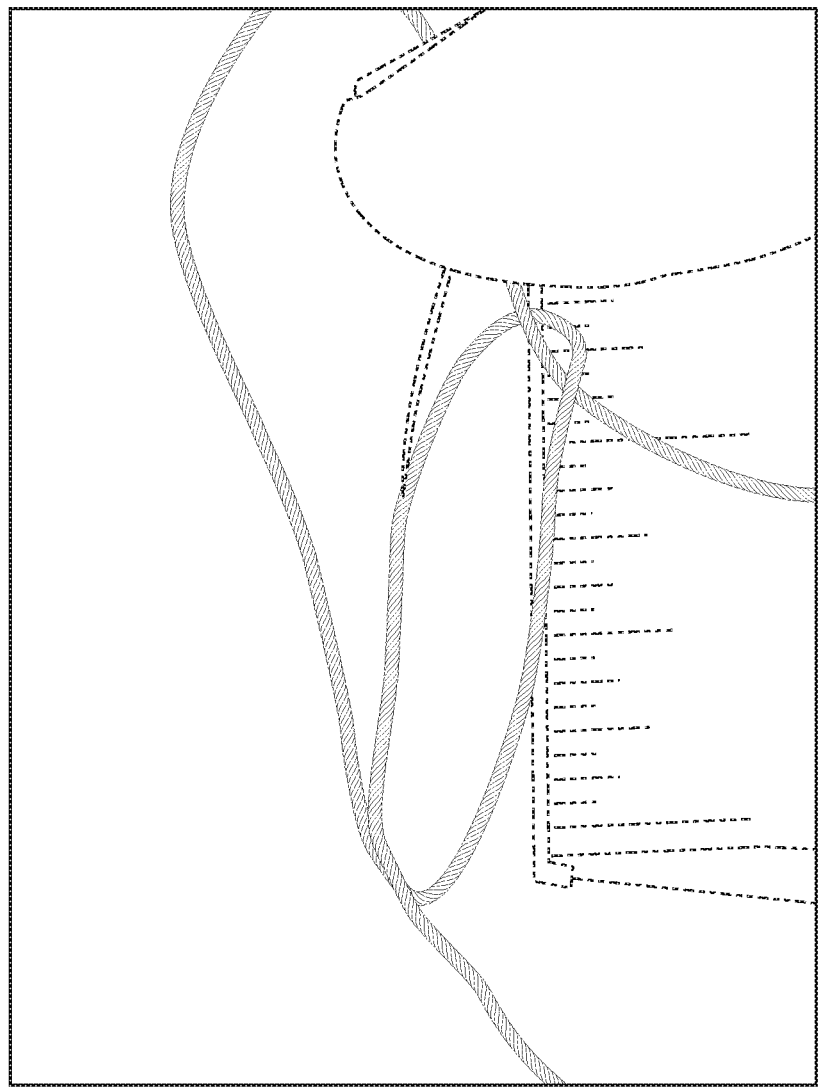

With reference to FIG. 10D, step 4, take the eyelet length desired, multiply it by two, and then measure to this length from location where the suture is first run through itself (from step 1).

Figure 10E:
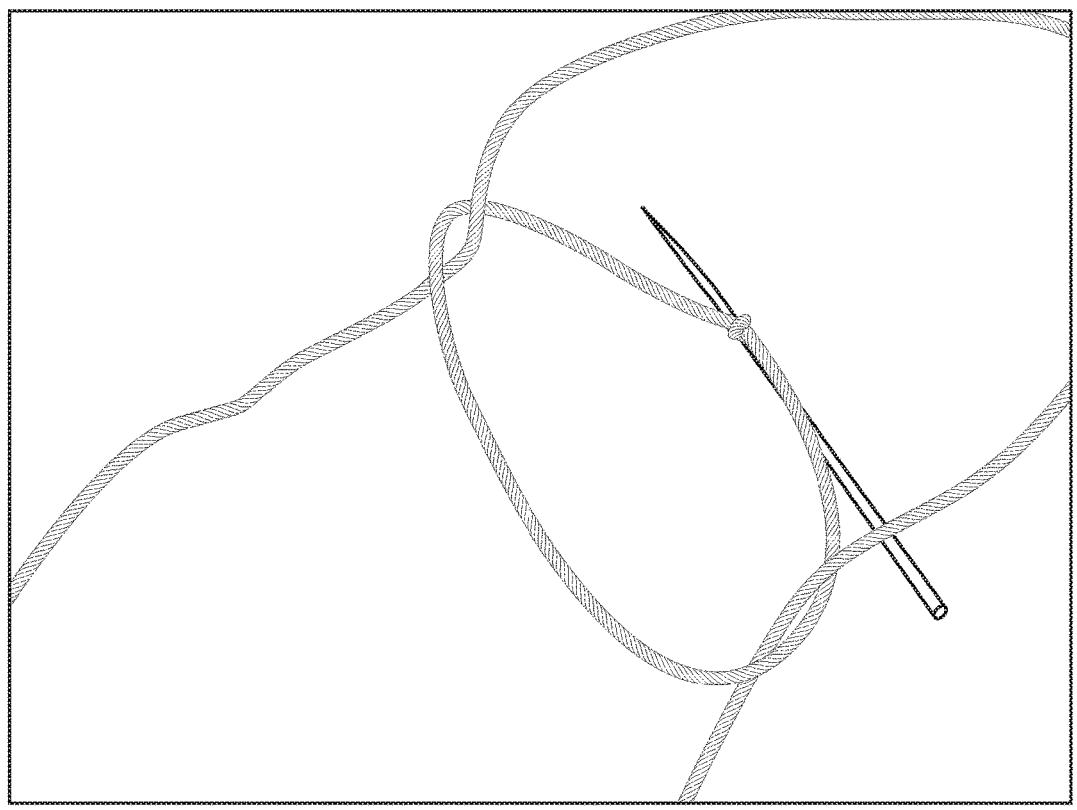

With reference to FIG. 10E, step 5, at the point measured to in step 4, thread the needle again through the inner diameter of the suture for about 1 mm (as in step 1). The needle should be facing towards the short end of the suture (as described in step 2). That is, if the needle were to run the rest of the length of the suture in that direction, it would emerge in the short length of suture. The suture will pass through this hole which the needle creates, in the same manner as the needle runs through. The end of the hole which was first pierced by the needle will be the end of the hole which long end of the suture is first passed through.

The foregoing steps create the unique knot of the suture eyelet. The tighter one pulls, the tighter the knot becomes. The two suture loops created by passing the suture through itself, are also looped together. The suture knot is tied through itself twice, creating two loops in opposite directions. These loops are also woven into each other. The primary mode of failure is for the suture to break from excess tension.

Figure 10F:
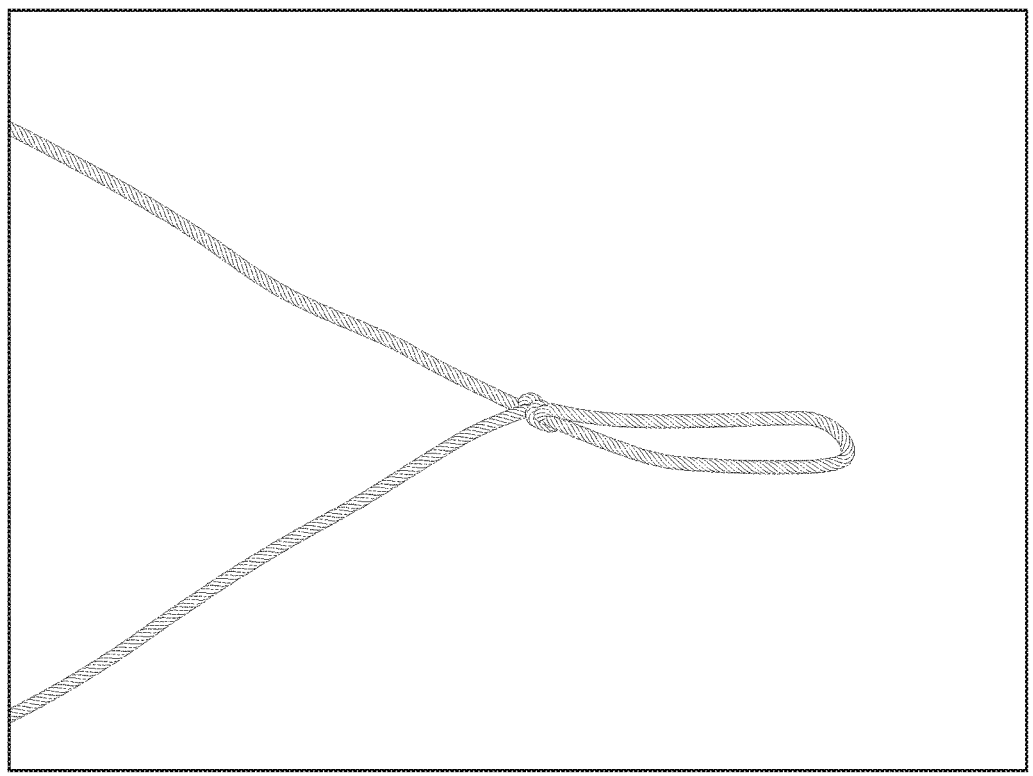

With reference to FIG. 10F, step 6, tighten both loops of the knot. The suture eyelet can now be used in a variety of ways.

Figure 10G:
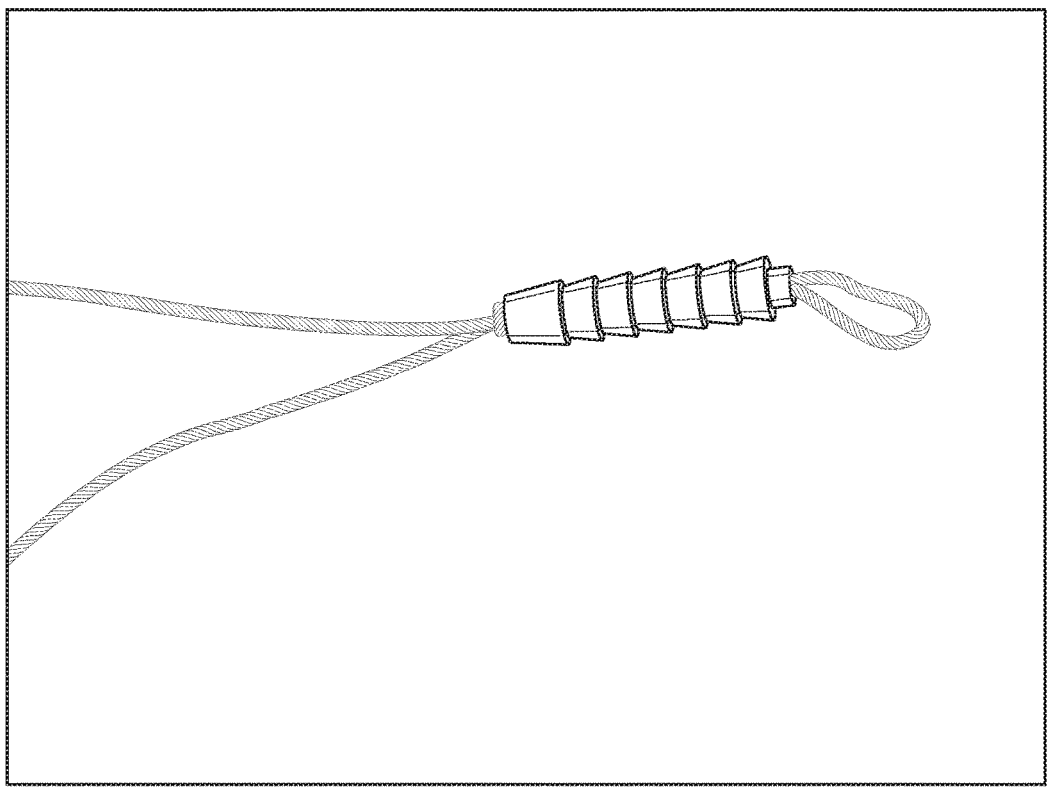

With reference to FIG. 10G, the suture eyelet is pulled through a cannulated suture anchor used for soft tissue repair (e.g., the cannulated suture anchor 400 of FIG. 9A-9C). The tips of the suture can be heat cut if needed.

Some examples of the suture anchors 100, 200, 400, 500, and 600 are small-diameter anchors or "microanchors" having diameters on the order of 1 mm to 3 mm. Other examples include larger diameter anchors for use in different parts of the body. Examples of the suture anchors 100, 200, 400, 500, and 600 may be completely or a portions thereof (e.g., the body) made from a formulation of poly(lactic-co-glycolic) acid (PLGA), β-Tricalcium phosphate (β-TCP) and calcium sulfate, poly-L-lactic acid-hydroxyapatite (PLLA-HA), polyether ether ketone (PEEK) or variants thereof. Biocomposite examples of suture anchors 100, 200, 400, 500, and 600 made from a combination of PLGA, β-TCP, and calcium sulfate are absorbable by the body, which is beneficial to natural healing. An example formulation of PLGA, β-TCP, and calcium sulfate is described in U.S. Pat. No. 8,545,866, the entirety of which is herein incorporated by reference. Other commonly used material for implants are also contemplated by this disclosure.

It is noted that the foregoing examples have been provided merely for the purpose of explanation and are in no way to be construed as limiting of the present invention. While the present invention has been described with reference to examples, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and examples, the present invention is not intended to be limited to the particulars disclosed herein; rather, the present invention extends to all functionally equivalent structures, methods and uses, such as are within the scope of the appended claims.

The invention claimed is:

1. A suture anchor for soft tissue repair, the suture anchor comprising:
    a body having a proximal end engageable with a suture anchor insertion instrument, a distal end, a longitudinal axis extending between the proximal end and the distal end, and an outer surface extending between the proximal and distal ends;
    a plurality of projections extending from the surface;
    a first bore extending completely across the body transverse to the longitudinal axis;
    a soft suture bridge threaded through the first bore and having first and second free ends extending proximally from the first bore; and
    a repair suture threaded through apertures at each of the first and second free ends so as to engage with the first and second free ends of the soft suture bridge, wherein each of the first and second free ends structurally defines all boundaries of an eyelet which defines a discretely bounded aperture at that end, the repair suture being threaded through the eyelets;
    wherein an initial size of each aperture is smaller than a cross-section of the repair suture and wherein each aperture is resiliently elastic such that a size thereof (i) increases when tension is applied to the repair suture thereby enabling the repair suture to slide relative to the aperture and (ii) decreases when tension is released thereby inhibiting the repair suture from sliding relative to the aperture.

2. The suture anchor of claim 1 wherein the proximal end of the body includes one of a protrusion or recess for engaging a complementary recess or protrusion, respectively, of the suture anchor insertion instrument.

3. The suture anchor of claim 1 wherein the distal end of the body terminates at a distal tip configured for inserting into a hole prepared in bone.

4. The suture anchor of claim 1 wherein the distal end of the body terminates at a distal tip configured for inserting into bone without a hole prepared in the bone.

5. The suture anchor of claim 1 wherein the projections include a plurality of annular ribs, wings, or a combination of annular ribs and wings.

6. The suture anchor of claim 1 wherein the eyelets are preformed and sized to permit the repair suture to slide, whereby the repair suture is slidably engaged with the first and second free ends.

7. The suture anchor of claim 6 wherein the soft suture bridge is configured and dimensioned so that, when the repair suture is tensioned such that the first and second free ends are fully extended proximally, the preformed eyelets are configured to align with one another along an axis transverse to the longitudinal axis and extending through a recess formed along an outer surface of the proximal end of body and extending transversely completely across the body.

8. The suture anchor of claim 6 wherein the soft suture bridge is configured and dimensioned so that, when the repair suture is tensioned so that the first and second ends are fully extended proximally, the preformed eyelets are configured to align with one another along an axis transverse to the longitudinal axis and proximal to the proximal end of the body.

9. The suture anchor of claim 1 wherein the soft suture bridge is a suture and the free ends of the suture are pierced by the repair suture thereby forming the apertures therethrough.

10. The suture anchor of claim 1 further comprising a pair of channels formed along an outer surface of the body and extending proximally from the first bore to the proximal-most point of the body.

11. The suture anchor of claim 10 further comprising a recess formed along an outer surface of the proximal end of the body and extending transversely completely across the body along an axis transverse to the longitudinal axis, the recess having a cross section larger than a cross section of the repair suture which permits the repair suture to slide; and
wherein the pair of channels extend between the first bore and the recess.

12. The suture anchor of claim 1 further comprising:
a second bore extending completely across the body transverse to the longitudinal axis and located proximal to the first bore; and
a cannulation extending, proximally, from the second bore along the longitudinal axis; and
wherein respective free ends of the suture bridge that extend out of opposite sides of the first bore are threaded through the opposite sides of the second bore into the cannulation and through the cannulation towards the proximal end of the body.

13. The suture anchor of claim 1 wherein the body further comprises at least one fenestration for facilitating bone ingrowth.

14. The suture anchor of claim 1 wherein the suture bridge is configured and dimensioned to hold the engaged repair suture at a predetermined fixed distance away from the first bore, when the repair suture is tensioned proximally so that the first and second ends are fully extended proximally and so that opposing ends of the repair suture extend proximally from the suture bridge.

15. The suture anchor of claim 1 wherein the body has a diameter between 1 mm and 3 mm.

16. The suture anchor of claim 1 wherein the body comprises a material selected from a formulation of poly (lactic-co-glycolic) acid (PLGA), β-Tricalcium phosphate (β-TCP) and calcium sulfate, poly-L-lactic acid hydroxyapatite (PLLA-HA), polyether ether ketone (PEEK) or variants thereof.

17. The suture anchor of claim 1 wherein the distal end of the body terminates in a top comprising a metal selected from titanium, stainless steel or variants thereof.

18. The suture anchor of claim 1 wherein the apertures are one of (i) preformed or (ii) formed by piercing the first and second free ends of the suture bridge with the repair suture.

19. A suture anchor system for soft tissue repair, the system comprising:
a suture anchor insertion instrument comprising:
a handle
a shaft extending from the handle; and
an inserter tip extending from the shaft and terminating at a distal terminal end;
and
a suture anchor disposed at the distal terminal end of the suture anchor insertion instrument, the suture anchor comprising:
a body having a proximal end engageable with the inserter tip of the suture anchor insertion instrument, a distal end, a longitudinal axis extending between the proximal end and the distal end, and an outer surface extending between the proximal end and the distal end;
a plurality of projections extending from the surface;
a bore extending completely across the body transverse to the longitudinal axis;
a soft suture bridge threaded through the bore and having first and second free ends extending proximally from the bore; and
a repair suture threaded through apertures at each of the first and second free ends so as to engage with the first and second free ends of the soft suture bridge, wherein each of the first and second free ends structurally defines all boundaries of an eyelet which defines a discretely bounded aperture at that end, the repair suture being threaded through the eyelets;
wherein an initial size of each aperture is smaller than a cross-section of the repair suture and wherein each aperture is resiliently elastic such that a size thereof (i) increases when tension is applied to the repair suture thereby enabling the repair suture to slide relative to the aperture and (ii) decreases when tension is released thereby inhibiting the repair suture from sliding relative to the aperture.

20. The system of claim 19 wherein the inserter tip comprises a longitudinal axis and a recess extending, proximally, from the distal terminal end towards the handle and along the longitudinal axis; and
wherein the proximal end of the body comprises a protrusion that is complementary to the recess of the suture anchor insertion instrument.

21. The system of claim 20 wherein the inserter tip comprises a passageway extending through the inserter tip and transverse to the longitudinal axis, the passageway configured to permit the repair suture to be routed, externally, along the outside of the inserter tip and the shaft.

22. A method of soft tissue repair, the method comprising:
inserting a suture anchor into bone, the suture anchor comprising: a body having a proximal end engageable with a suture anchor insertion instrument, a distal end, a longitudinal axis extending between the proximal end and the distal end, and an outer surface extending between the proximal and distal ends;
a plurality of projections extending from the surface;
a bore extending completely across the body transverse to the longitudinal axis; and
a soft suture bridge having first and second free ends through which a repair suture can be fed, the soft suture bridge passing through the bore with the first and second free ends extending proximally from the bore, wherein each of the first and second free ends structurally defines all boundaries of an eyelet which defines a discretely bounded aperture at that end, the repair suture being threaded through the eyelets;
wherein an initial size of each aperture is smaller than a cross-section of the repair suture and wherein each aperture is resiliently elastic such that a size thereof (i) increases when tension is applied to the repair suture thereby enabling the repair suture to slide relative to the aperture and (ii) decreases when tension is released thereby inhibiting the repair suture from sliding relative to the aperture; and
sliding the repair suture through the soft suture bridge to tie a knot in the repair suture and attach soft tissue to the bone, whereby the soft suture bridge is dimensioned and configured to hold the repair suture at a predetermined fixed distance away from the bore, when the suture is tensioned proximally so that the first and second free ends are fully extended proximally and so that opposing ends of the repair suture extend proximally from the suture bridge.

23. The method of claim 22 further comprising drilling a hole into the bone; and wherein inserting the suture anchor includes inserting the suture anchor into the hole.

24. The method of claim 22 further comprising repositioning the soft tissue by sliding the repair suture through the soft suture bridge.

* * * * *